(12) United States Patent
Ma et al.

(10) Patent No.: US 12,427,168 B2
(45) Date of Patent: Sep. 30, 2025

(54) EXTRACELLULAR VESICLE AND USE THEREOF IN SKIN PRODUCTS

(71) Applicant: EV CELL BIOTECH (GUANGZHOU) CO., LTD., Guangzhou (CN)

(72) Inventors: Lan Ma, Guangzhou (CN); Xiaoxing Kou, Guangzhou (CN); Songtao Shi, Guangzhou (CN)

(73) Assignee: EV CELL BIOTECH (GUANGZHOU) CO., LTD., Guangzhou (CN)

( * ) Notice: Subject to any disclaimer, the term of this patent is extended or adjusted under 35 U.S.C. 154(b) by 706 days.

(21) Appl. No.: 17/793,833

(22) PCT Filed: Jan. 20, 2021

(86) PCT No.: PCT/CN2021/072937
§ 371 (c)(1),
(2) Date: Jul. 19, 2022

(87) PCT Pub. No.: WO2021/147922
PCT Pub. Date: Jul. 29, 2021

(65) Prior Publication Data
US 2023/0084480 A1    Mar. 16, 2023

(30) Foreign Application Priority Data

Jan. 20, 2020  (CN) .......................... 202010066154.6
Jan. 20, 2020  (CN) ........................ 202010067658.X

(51) Int. Cl.
| | |
|---|---|
| A61K 35/28 | (2015.01) |
| A61K 8/98 | (2006.01) |
| A61K 31/155 | (2006.01) |
| A61K 31/553 | (2006.01) |
| A61K 35/545 | (2015.01) |
| A61K 45/06 | (2006.01) |
| A61P 17/02 | (2006.01) |
| A61Q 7/00 | (2006.01) |
| C12N 5/0775 | (2010.01) |

(52) U.S. Cl.
CPC ................ *A61K 35/28* (2013.01); *A61K 8/98* (2013.01); *A61K 31/155* (2013.01); *A61K 31/553* (2013.01); *A61K 35/545* (2013.01); *A61K 45/06* (2013.01); *A61P 17/02* (2018.01); *A61Q 7/00* (2013.01); *C12N 5/0662* (2013.01)

(58) Field of Classification Search
None
See application file for complete search history.

(56) References Cited

U.S. PATENT DOCUMENTS

| | | |
|---|---|---|
| 2014/0364588 A1 | 12/2014 | Haugwitz et al. |
| 2015/0086639 A1 | 3/2015 | Huang |
| 2017/0216364 A1 | 8/2017 | Shi et al. |
| 2018/0055894 A1 | 3/2018 | Kim et al. |
| 2018/0066307 A1 | 3/2018 | Ter-Ovanesyan et al. |
| 2018/0256490 A1 | 9/2018 | Kim et al. |
| 2018/0371418 A1 | 12/2018 | Yang et al. |

FOREIGN PATENT DOCUMENTS

| | | |
|---|---|---|
| CN | 102892781 A | 1/2013 |
| CN | 106289926 A | 1/2017 |
| CN | 106659740 A | 5/2017 |
| CN | 107567329 A | 1/2018 |
| CN | 107750161 A | 3/2018 |
| CN | 107893050 A | 4/2018 |
| CN | 108070645 A | 5/2018 |
| CN | 108367032 A | 8/2018 |
| CN | 109293780 A | 2/2019 |
| CN | 109701065 A | 5/2019 |
| CN | 109893515 A | 6/2019 |
| CN | 110123840 A | 8/2019 |
| CN | 111494417 A | 8/2020 |
| JP | 2004-500407 A | 1/2004 |
| JP | 2018-522071 A | 8/2018 |
| WO | 2019/146612 A1 | 8/2019 |
| WO | 2019/212293 A1 | 11/2019 |

OTHER PUBLICATIONS

Darwin et al., "Alopecia Areata: Review of Epidemiology, Clinical Features, Pathogenesis, and New Treatment Options", International Journal Trichology, vol. 10, issue 2, pp. 51-60, Apr. 30, 2018 (11 pages total).

International Search Report, dated Apr. 23, 2021, from the International Authority in International Application No. PCT/CN2021/072937.

Written Opinion, dated Apr. 23, 2021, from the International Authority in International Application No. PCT/CN2021/072937.

Kaitlin Clark et al., "Placental Mesenchymal Stem Cell-Derived Extracellular Vesicles Promote Myelin Regeneration in an Animal Model of Multiple Sclerosis." Cells, vol. 8, Issue 12, No. 1497. Nov. 23, 2019 (16 pages).

(Continued)

*Primary Examiner* — Michael V Meller
(74) *Attorney, Agent, or Firm* — Sughrue Mion, PLLC

(57) ABSTRACT

Use of an inducible extracellular vesicle as a medicament for skin, health care products or skin care products. A composition, comprising the inducible vesicle and the medicaments or care products for skin.

12 Claims, 21 Drawing Sheets

(56) References Cited

OTHER PUBLICATIONS

Hiroaki Haga et al., "Extracellular vesicles from bone marrow derived mesenchymal stem cells protect against murine hepatic ischemia-reperfusion injury." Liver Transplantation, vol. 23, Issue 6, pp. 791-803. May 26, 2017 (40 pages).

Ruenn Chai Lai et al. "MSC secretes at least 3 EV types each with a unique permutation of membrane lipid, protein and RNA." Journal of Extracellular Vesicles, vol. 5, No. 29628. Feb. 24, 2016 (12 pages).

Zhen Weng et al. "Research progress on detection and identification of exosomes and their role in coagulation." Modern Medical Journal, vol. 47, Issue 5, 614-618. Jul. 30, 2019 (11 pages).

CD34

CD45

CD9

CD63

CD81

Annexin V iPSC IEVs

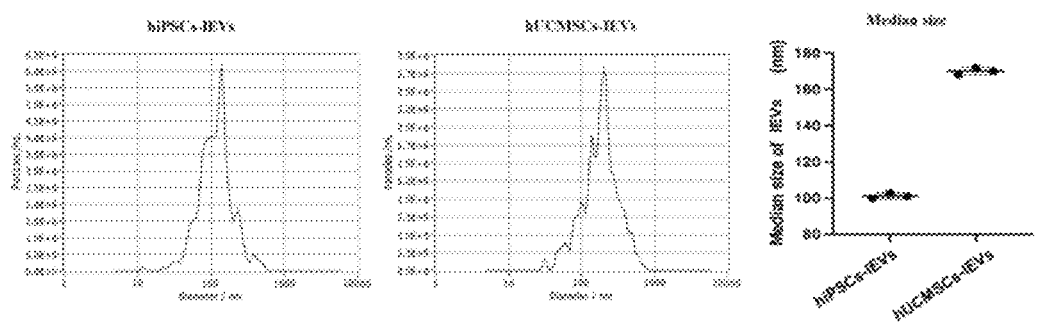
FIG. 21
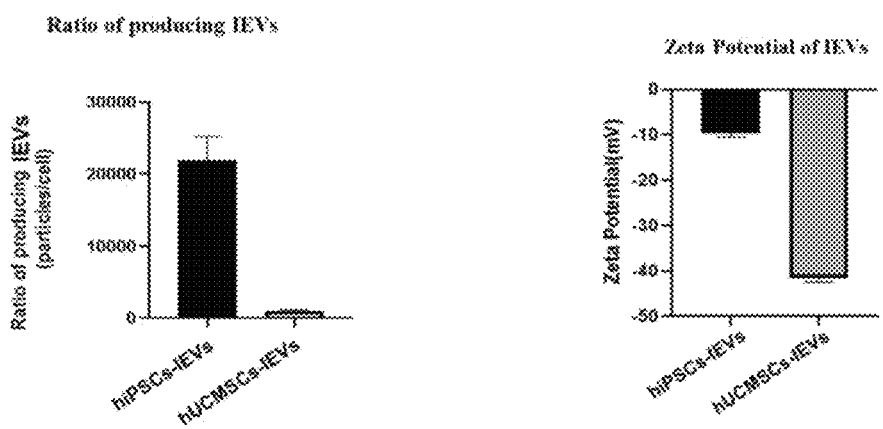
FIG. 22
FIG. 23
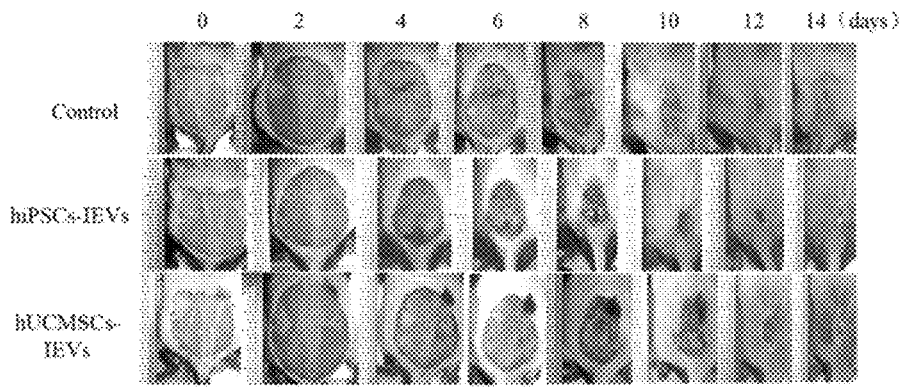
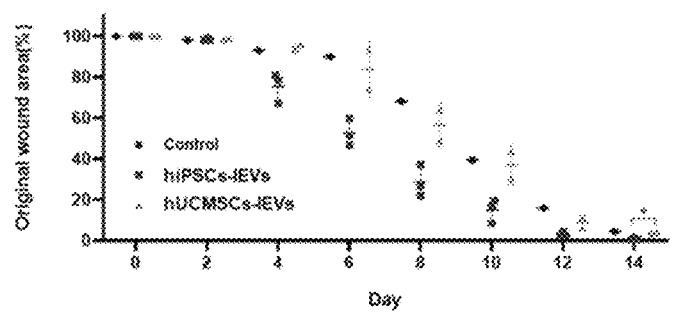
FIG. 24

EXTRACELLULAR VESICLE AND USE THEREOF IN SKIN PRODUCTS

CROSS-REFERENCE TO RELATED APPLICATION

This application is the national phase application of International Application No. PCT/CN2021/072937, filed Jan. 20, 2021, which claims priorities to Chinese Patent applications Ser. No. 202010067658.X and No. 202010066154.6, both filed on Jan. 20, 2020, in China National Intellectual Property Administration, and respectively entitled "Extracellular Vesicle and Use thereof in Skin Products" and "Vesicle and Use thereof", of the contents of each of which are hereby incorporated by reference in its entirety.

TECHNICAL FIELD

The present disclosure belongs to the technical field of biomedicine, and relates to an extracellular vesicle and use thereof in skin products.

BACKGROUND ART

Extracellular vesicles (EVs) are nanoscale carriers containing proteins, nucleic acids and various cytokines secreted by cells. Extracellular vesicles can act on target cells in an endocrine or paracrine manner, and play an important role in the process of substance transmission and information exchange between cells. It has been found that the information exchange mediated by extracellular vesicles is of great significance for regulation in the physiological or pathological process, involving immune regulation, tumor growth, angiogenesis, injury repair, etc. At present, studies in this field mainly focus on exosomes. Exosomes are extracellular vesicles with a diameter of about 30-150 nm, containing RNA, lipids, proteins, etc. Exosomes are widely involved in the various physiological/pathological regulations of the body, and can be used for diagnosis, treatment and prognosis assessment of a variety of diseases. So far, mesenchymal stem cells (MSCs) have been considered to be the most potent cells for producing exosomes. Numerous studies have found that MSCs-derived exosomes can mimic the biological function of MSCs, and play an important part in regulation in promoting cell growth and differentiation and repairing tissue defects. Therefore, cell vesicle therapy based on MSCs-derived exosomes has achieved remarkable development in recent years. However, current exosomes-based cell vesicle therapies still have many problems, such as complex exosome extraction and purification, time-consuming, high requirements for equipment and reagents, low physiological exosome production, and so on, which limit the clinical transformation and application of exosome therapies.

There are many diseases that cause hair loss, and the most common one is alopecia areata. Alopecia areata, commonly known as "ghost shaving", is a sudden onset of localized hair loss in patches, with normal local skin and no subjective symptoms. At present, the etiology is unknown. Pathological examination shows decreased hair follicles, and lymphocyte infiltration around hair follicles, and this disease is sometimes combined with other autoimmune diseases (Alopecia Areata: Review of Epidemiology, Clinical Features, Pathogenesis, and New Treatment Options. Darwin E, Hirt P A, Fertig R, Doliner B, Delcanto G, Jimenez J J. Int J Trichology. 2018; 10(2):51-60). Most alopecia areata have a tendency to heal naturally, while a few cases recur, so the treatment is difficult, but there are many therapies for combined treatment of alopecia. It can occur at any age, but mostly in young adults. There is no significant difference in incidence of both sexes. Skin lesions are presented as round or oval non-scarring hair hoss with "exclamation point hairs" observed on the periphery of the patches. The complete or nearly complete loss of hair on the scalp is called alopecia totalis. The complete loss of all hair (including body hair) is called alopecia universalis, and alopecia serpiginosa is also be seen. There is no abnormality of skin except hair loss. It has been reported that alopecia areata (AA) models can be established by topical application of imiquimod in C3H/HeJ mice, but there is no effective treatment for alopecia areata.

SUMMARY OF THE INVENTION

In an aspect, use of an induced vesicle in preparation of or as a skin product or skin appendage product is provided.

In this disclosure, a "skin product" refers to a product that acts on the skin, e.g. a product that acts on the skin to treat, improve, repair, remove wrinkle, or remove a wound, either directly or indirectly, and can be a drug, a drug carrier, a food, a health care product, a skin care product, or a medical cosmetology product.

In some embodiments, the product is: a drug, a drug carrier, food, a health-care product, a skin-care product, or a medical and medical cosmetology product.

In some embodiments, the skin is epidermal, dermal, or subcutaneous tissues.

In some embodiments, the skin appendage is hair on the body and scalp, sweat glands, sebaceous glands, nails, or toenails.

During the course of the study, the inventors accidentally found that when IEVs were injected into nude mice, they were not distributed in the heart, kidney and brain, but distributed in the nail, presumably related to the targeting of IEVs.

After further studies, the inventors have found that IEVs have a good therapeutic effect on hair regrowth and wound healing. On the one hand, IEVs have a therapeutic effect on the skin or skin appendages, and on the other hand, they just target the skin or skin appendages, making it especially suitable for preparation or application as a skin product or skin appendage product.

In one aspect, a composition is provided, comprising: an induced vesicle, and a skin medicament or skin conditioner.

In some embodiments, the skin medicament and the skin conditioner are encapsulated in an extracellular vesicle, or are separately present in the composition.

In some embodiments, the dosage form of the composition is preferably selected from the group consisting of a lyophilized powder needle, an injection, a tablet, a capsule, or a patch; and in some embodiments, the patch is selected from a microneedle patch; and in some embodiments, the dosage form is selected an injection or a microneedle patch.

In some embodiments, the induced vesicle is a vesicle produced by inducing apoptosis of normally viable stem cells by external impacts; in some embodiments, the induced vesicle is produced by inducing stem cells or apoptosis of stem cells by addition of Staurospora, ultraviolet irradiation, starvation, or thermal stress, or a combination of one or more thereof.

In an aspect, a composition is provided, comprising: a first reagent consisting of a stem cell or stem cell extracellular vesicle; and, a second reagent consisting of an anti-aging substance or a positive regulator for Wnt signaling pathways.

In some embodiments, the extracellular vesicle refers to a subcellular product, also referred to as an induced vesicle, that is produced by intervening or inducing apoptosis of precursor cells (e.g. stem cells, especially mesenchymal stem cells) which are normally viable. Preferably, the precursor cells are early precursor cells.

Such subcellular product typically has a membrane structure and contains the genetic material DNA, and is non-dividing, mobile and migratory. It is a class of substances between cells and extracellular vesicles (apoptotic bodies, exosomes, etc.).

In some embodiments, the stem cells are selected from one or more of induced pluripotent stem cells, blood stem cells, bone marrow mesenchymal stem cells, urine mesenchymal stem cells, oral mesenchymal stem cells, adipose mesenchymal stem cells, placental mesenchymal stem cells, umbilical cord mesenchymal stem cells, periosteal mesenchymal stem cells, and skin mesenchymal stem cells.

In some embodiments, the stem cells are selected from one or more of induced pluripotent stem cells, blood stem cells, bone marrow mesenchymal stem cells, adipose mesenchymal stem cells, umbilical cord mesenchymal stem cells, oral mesenchymal stem cells, and skin mesenchymal stem cells.

In some embodiments, the stem cells are selected from one or more of induced pluripotent stem cells, umbilical cord mesenchymal stem cells, blood stem cells or bone marrow mesenchymal stem.

In some embodiments, the stem cell extracellular vesicle is selected from one or more of exosomes, migrants, microbubbles, apoptotic bodies, and induced extracellular vesicles.

In some embodiments, the stem cell extracellular vesicle is selected from an induced extracellular vesicle.

In some embodiments, the anti-aging substance is selected from one or more of metformin, and resveratrol.

In some embodiments, the anti-aging substance is selected from metformin.

In some embodiments, the Wnt signaling pathways are selected from Wnt/β-catenin pathways.

In some embodiments, the positive regulator is selected from an agonist. In some embodiments, the agonist is selected from one or more of Licl, CHIR99021, SB-216763, BIO, Wnt Agonist or WAY 262611; more preferably Licl.

In some embodiments, the agonist is selected from Licl.

In some embodiments, the positive regulator is selected from a notice for performing exercises.

In some embodiments, the notice is selected from one or more of a package, a label, or instructions for use.

In some embodiments, the composition comprises the stem cell or stem cell extracellular vesicle and the anti-aging substance in a ratio of $(0.5-5)\times10^7$ by count:(0.05-10) mg.

In some embodiments, the composition comprises $1\times10^7$ to $3\times10^7$ by count of the stem cell or stem cell extracellular vesicle; and 0.1-5 mg of the anti-aging substance.

In some embodiments, the composition comprises $1.8\times10^7$ to $2.7\times10^7$ by count of the stem cell or stem cell extracellular vesicle.

In some embodiments, the composition comprises 0.2-3 mg of the anti-aging substance.

In use of the composition, the extracellular vesicle may optionally be administered in a route selected from the group consisting of intravenous injection, intramuscular injection, subcutaneous injection, intrathecal injection or infusion, and intraorgan infusion. For example, for intravenous injection, tail vein injection may be used. Intraorgan infusion includes infusion into anatomical spaces such as, by way of example, the gall bladder, gastrointestinal lumen, esophagus, pulmonary system (by inhalation), and/or bladder.

As an example, for intraperitoneal injection in gastrointestinal infusion, a good therapeutic effect can also be obtained by intraperitoneal injection as compared with tail vein injection. Intraperitoneal injection is superior to tail vein injection in safety and maneuverability.

In some embodiments, the two reagents of the composition are provided in the form of a single pharmaceutical composition, and in some embodiments, a kit or combined dispenser package comprising each of the two reagents is contemplated. It should be understood that the present disclosure encompasses co-administration of either of the two reagents to a subject, whether such administration is in a single formulation or in a combination of separate formulations, and whether such administration is simultaneous or staggered.

In some embodiments, the extracellular vesicle is produced by inducing apoptosis of mesenchymal stem cells by the addition of Staurosporine, ultraviolet irradiation, starvation, thermal stress, or a combination thereof.

In some embodiments, the extracellular vesicle is produced by inducing apoptosis of mesenchymal stem cells by the addition of Staurosporine.

In some embodiments, the passage number of the mesenchymal stem cells may be 2-5 passages, but is not limited thereto.

In some embodiments, the concentration of Staurosporine is greater than or equal to 1 nM; preferably in a range of 1-15000 nM; preferably in a range of 200-10000 nM; preferably in a range of 250-1000 nM; and preferably in a range of 500-1000 nM. In addition, the concentration of Staurosporine may be 280-9000 nM; may also be 230-8500 nM; may also be 500-1000 nM; may also be 500-900 nM; and may also be 500-800 nM. In some embodiments, the concentration of Staurosporine is 500 nM.

In some embodiments, the induced extracellular vesicle has a diameter of 0.45 μm or less. In some embodiments, the induced extracellular vesicle has a diameter of 0.05-0.45 μm. In some embodiments, the induced extracellular vesicle has a diameter of 0.1-0.45 μm. In some embodiments, the induced extracellular vesicle has a diameter of 0.1-0.35 μm. In some embodiments, the induced extracellular vesicle has a diameter of 0.15-0.35 μm. In some embodiments, the induced extracellular vesicle has a diameter of 0.15-0.3 μm. In some embodiments, the induced extracellular vesicle has a diameter of 0.15-0.2 μm. In some embodiments, the induced extracellular vesicle has a diameter of 0.05-0.4 μm. In some embodiments, the induced extracellular vesicle has a diameter of 0.05-0.38 μm. In some embodiments, the induced extracellular vesicle has a diameter of 0.05-0.35 μm. In some embodiments, the induced extracellular vesicle has a diameter of 0.05-0.32 μm. In some embodiments, the induced extracellular vesicle has a diameter of 0.05-0.3 μm. In some embodiments, the induced extracellular vesicle has a diameter of 0.05-0.25 μm. In some embodiments, the induced extracellular vesicle has a diameter of 0.05-0.22 μm. In some embodiments, the induced extracellular vesicle has a diameter of 0.15-0.22 μm. In some embodiments, the induced extracellular vesicle also may have a diameter of 0.15-0.45 μm, and may have a diameter of 0.2-0.3 μm.

In some embodiments, the induced extracellular vesicle has a marker Syntaxin 4. In some embodiments, the induced extracellular vesicle has a high expression of the marker Syntaxin 4. In some embodiments, the expression level of the marker Syntaxin 4 in the induced extracellular vesicles is higher than that in MSCs or exosomes. In some embodiments, the expression level of the marker Syntaxin 4 is 3-6 fold of that in exosomes derived from mesenchymal stem cells. In some embodiments, the expression level of the marker Syntaxin 4 is 3.5-5 fold of that in exosomes derived from mesenchymal stem cells. In some embodiments, the expression level of the marker Syntaxin 4 is 4.45 fold of that in exosomes derived from mesenchymal stem cells. In some embodiments, the marker further includes one or more of Annexin V, Flotillin-1, Cadherin 11, and Integrin alpha 5. In some embodiments, the marker is a combination of Syntaxin 4, Annexin V, Flotillin-1, Cadherin 11, and Integrin alpha 5. In some embodiments, the induced extracellular vesicle has a high expression of the markers Annexin V, Flotillin-1, Cadherin 11, and Integrin alpha 5. In some embodiments, the expression levels of the markers Annexin V, Flotillin-1, Cadherin 11, and Integrin alpha 5 in the induced extracellular vesicle are higher than that in MSCs or exosomes. In some embodiments, the expression levels of the markers Annexin V, Flotillin-1, Cadherin 11, and Integrin alpha 5 in the induced extracellular vesicle are 1-2 fold, 2-3 fold, 1-3 fold and 3-4 fold, respectively, of that in exosomes derived from mesenchymal stem cells. In some embodiments, the expression levels of the markers Annexin V, Flotillin-1, Cadherin 11, and Integrin alpha 5 in the induced extracellular vesicle are 1.5-2 fold, 2.5-3 fold, 1.5-2.5 fold and 3.5-4 fold, respectively, of that in exosomes derived from mesenchymal stem cells. In some embodiments, the expression levels of the markers Annexin V, Flotillin-1, Cadherin 11, and Integrin alpha 5 in the induced extracellular vesicle are 1.76 fold, 2.81 fold, 2.41 fold, 3.68 fold, respectively, of that in exosomes derived from mesenchymal stem cells. The induced extracellular vesicle described in the present disclosure are substantially different from exosomes, for example, the induced extracellular vesicle described in the present disclosure, IEVs, has a high expression of Syntaxin 4, and the expression levels of Annexin V, Flotillin-1, Cadherin 11, and Integrin alpha 5 in the induced extracellular vesicle are significantly higher than that in exosomes (see Example 3). In addition to the differences in marker expression, the induced extracellular vesicle IEVs also exhibits functional or therapeutic effects that are distinct from stem cells and other extracellular vesicles such as exosomes. In some embodiments, the induced extracellular vesicle also expresses CD29, CD44, CD73, CD166; and does not express CD34 and CD45. In some embodiments, the induced extracellular vesicle also expresses one or more of CD9, CD63, CD81 and C1q.

In some embodiments, use of the composition described above in manufacture of medicaments for promoting hair regrowth or wound healing is further provided.

In some embodiments, the composition further comprises a pharmaceutically acceptable carrier; and the dosage form of the composition is preferably selected from the group consisting of a lyophilized powder needle, an injection, a tablet, a capsule, or a patch.

In some embodiments, the patch is selected from a microneedle patch; and in some embodiments, the dosage form is selected an injection, a microneedle patch, or a tablet.

In some embodiments, a method for preparing the stem cell extracellular vesicle is further provided, comprising the following steps:
1) culturing mesenchymal stem cells in vitro, and washing the cells at 80%-90% confluence 2-5 times with PBS;
2) adding the mesenchymal stem cells prepared in step 1) into a serum-free medium containing 500-1000 nM Staurosporine, incubating at 37° C. for 16-24 h, and collecting the cell supernatant;
3) centrifuging the cell supernatant collected in step 2) at 500-15000 g for 5-30 min at 4° C., and collecting the supernatant;
4) centrifuging the cell supernatant collected in step 3) at 1500-2500 g for 5-30 min at 4° C., and collecting the supernatant;
5) centrifuging the cell supernatant collected in step 4) at 10000-30000 g for 15-60 min at 4° C., and obtaining the resulting pellet as the extracellular vesicle; and in some embodiments, the method further comprises a step of washing the extracellular vesicle; and in some embodiments, the washing step specifically comprises:
6) resuspending the extracellular vesicle prepared in step 5) in PBS, centrifuging at 10000-30000 g for 15-60 min at 4° C., and obtaining the resulting pellet as the extracellular vesicle.

In an aspect, use of an anti-aging substance in preparation of a concomitant drug for stem cell administration is further provided.

The "stem cell administration" in the embodiments of the present disclosure includes, but is not limited to, products or methods that enable stem cells or stem cell vesicles to enter an animal.

As an illustrative example, products that enable the administration of stem cells into an animal include lyophilized powders, injections, tablets, capsules or patches.

As an illustrative example, methods for administering a stem cell product into an animal include oral administration, injection, application, painting, sprinkling, and instillation.

The "concomitant drug" in the embodiments of the disclosure includes a drug that enters the body with another drug or drugs. The concomitant drugs may enter the body simultaneously or nearly simultaneously.

As an illustrative example, nearly simultaneous entries may be one after the other; or into the body at different times on the same day. For example, multiple reagents or their active ingredients may be prepared into one formulation, or two or more formulations may enter the body at least substantially simultaneously, for example, within about one hour of each other.

In some embodiments, the stem cell administration is a stem cell or stem cell extracellular vesicle.

In some embodiments, the stem cell administration is a stem cell or stem cell extracellular vesicle for ingestion into an animal; preferably, the animal is a mammal; preferably, the mammal is a human.

In an aspect, a stem cell administration system is provided, comprising: the stem cell administration, and a concomitant drug; the concomitant drug is selected from one or two of an anti-aging substance or a positive regulator for Wnt signaling pathways; the stem cell administration comprises a stem cell or stem cell extracellular vesicle; and the anti-aging substance or the positive regulator for Wnt signaling pathways are as described above.

In an aspect, use of a stem cell or stem cell extracellular vesicle in preparation of medicaments for promoting hair regrowth or wound healing through metabolism of the stem cell or stem cell extracellular vesicle regulated by Wnt signaling pathways is further provided.

In some embodiments, the medicament for promoting hair regrowth or wound healing comprises a stem cell or stem cell extracellular vesicle; and an anti-aging substance. The stem cell or stem cell extracellular vesicle and the anti-aging substance are as previously described.

In an aspect, a method of promoting excretion of a stem cell administration from the body of an animal, or hair regrowth, or wound healing is provided, the method comprising during the administration of the stem cell administration, simultaneously or nearly simultaneously administering the anti-aging substance, or performing exercises.

In some embodiments of the present disclosure, the "positive regulator for Wnt signaling pathways" includes, but is not limited to, agents or methods that upregulate and activate Wnt, such as agonists. The implementations of the foregoing "method" include prompts, instructions, prescriptions, orders, and the like, to the subject.

In an aspect, a method of treating a skin or skin appendage disease is also provided, comprising the steps of: administering the induced vesicle, composition, stem cell administration system described above to a subject in need thereof.

In some embodiments, the skin or skin appendage disease is selected from the group consisting of wounds, alopecia, scars, burns and scalds, or ulcers. In some embodiments, the wounds are selected from resection wounds, cuts, puncture wounds, or piercing wounds.

Induced pluripotent stem cells include pluripotent stem cells formed by reprogramming terminally differentiated somatic cells by introducing specific transcription factors.

BRIEF DESCRIPTION OF THE DRAWINGS

FIG. 4A shows particle diameter distribution of flow cytometry of IEVs; FIG. 4B shows the scattered light intensity of Side Scatter (SSC) analysis of IEVs, indicating the particle diameter distribution of the IEVs. FIG. 4C shows the scattered light intensity of IEVs analyzed by standardized small particle microspheres produced by Bangs Laboratories, indicating the particle diameter distribution of IEVs; FIG. 4D shows IEVs observed by transmission electron microscopy (TEM), indicating the particle diameter distribution of IEVs; FIG. 4E shows Nanoparticle Tracking Analysis (NTA), indicating the particle diameter distribution of IEVs; FIG. 4F shows particle size measurements of IEVs at the single-vesicle level using a nano-flow cytometry technique, indicating the particle diameter distribution of IEVs.

FIG. 6A shows the results of proteomic quantitative analysis of MSCs, MSCs-Exosomes and MSCs-IEVs by the DIA quantitative technique; FIG. 6B shows a heat map drawn by screening for IEVs-specific highly expressed proteins. FIG. 6C shows the results of GO enrichment analysis of differential proteins, indicating the expressions of Annexin V, Flotillin-1, Cadherin 11, Integrin alpha 5, and Syntaxin 4 molecules in IEVs. FIG. 6D shows the results of Western Blot verification of the expressions of Annexin V, Flotillin-1, Cadherin 11, Integrin alpha 5, and Syntaxin 4 in MSCs, MSCs-Exosomes, and MSCs-IEVs;

FIGS. 21-23 show, in order, the particle size, yield, and potential of hiPSCs-IEVs and hUCMSCs-IEVs characterized by NTA as described in Example 12;

FIG. 24 shows the wound and area of wound at different time points for different treatment groups in the skin injury model of Example 12.

DETAILED DESCRIPTION

Figure 1:
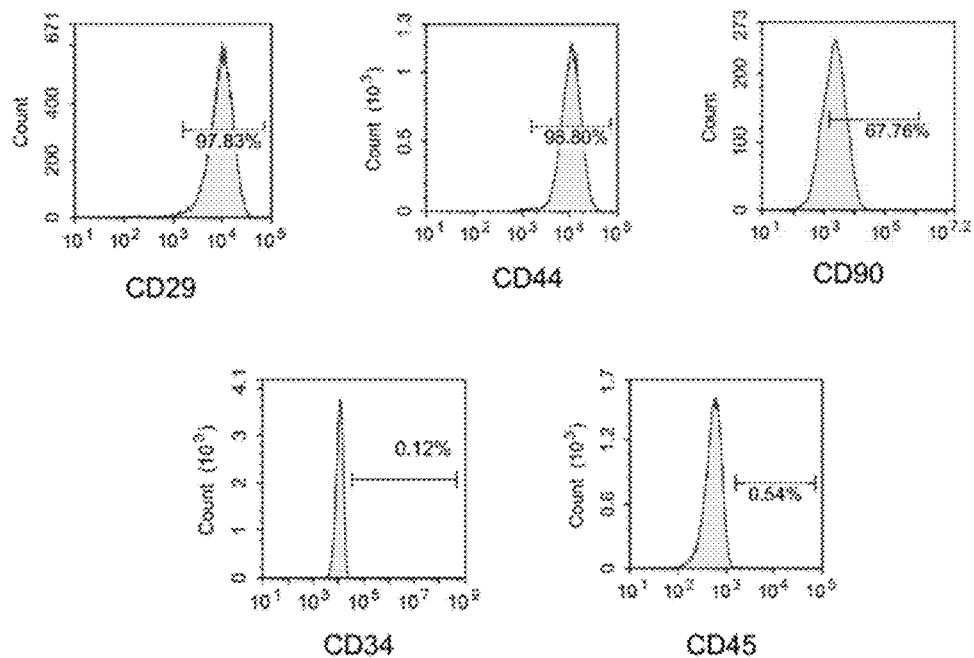
FIG. 1 illustrates flow cytometry of Example 1.

The embodiments of the present disclosure are further illustrated by the following specific examples, which are not intended to limit the scope of the disclosure. Certain insubstantial modifications and adaptations made by others in light of the disclosed concepts remain within the scope of the disclosure.

The IEVs in the examples of the present disclosure is an abbreviation for induced vesicles, and induced extracellular vesicles (IEVs). Induced extracellular vesicles refer to a class of subcellular products that are disrupted or induced to undergo apoptosis when precursor cells (e.g. stem cells) normally survive. Such subcellular product generally has a membrane structure, expresses apoptotic markers, and partially contains the genetic material DNA. The inventors have found that the induced extracellular vesicle is a substance that distinguishes between cells and conventional extracellular vesicles (e.g. exosomes, etc.). In some embodiments, normal viable cells are, for example, non-apoptotic cells, non-senescent cells, non-senescent cells with arrested proliferation, non-post-cryopreservation cells, non-malignant cells with abnormal proliferation, or non-damaged cells, etc. In some embodiments, the normally viable cells are taken from cells at 80-100% confluence in the cell culture process. In some embodiments, the normally viable cells are taken from cells in the log phase. In some embodiments, the normally viable cells are taken from primary culture cells derived from a human or murine tissues and subculture cells thereof. In some embodiments, the normally viable cells are taken from an established cell line or cell strain. In some embodiments, the precursor cells are taken from early cells.

In the present disclosure, IEV equals to IEVs.

In the present disclosure, STS refers to Staurosporine.

In the present disclosure, the components of the "composition" may be present in admixture or may be packaged separately. Separately packaged components may also contain their respective adjuvants. The adjuvant refers to a means used in pharmacy to aid the therapeutic efficacy of a drug. Where the components of the composition are packaged separately, the separately packaged components may be administered simultaneously or sequentially in any order where the patient is first treated with one drug and then administered with another drug. The patient refers to a mammalian subject, particularly a human subject.

In the present disclosure, the "composition" may also be present such that one component is encapsulated by another component. In some embodiments, in the composition, the induced vesicle serves as a drug carrier, and a drug for treating or preventing a disease is encapsulated in the induced vesicle.

"Comprises" or "comprising" is intended to mean that the compositions (e.g. media) and methods include the recited elements, but do not exclude other elements. When used to define compositions and methods, "consisting essentially of" means excluding other elements of any significance to the combination for the stated purpose. Thus, a composition substantially consisting of the elements defined herein does not exclude other materials or steps that do not substantially affect the basic and novel features of the claimed disclosure. "Consisting of" means excluding trace elements of other components and substantial method steps. Embodiments defined by each of these transition terms are within the scope of this disclosure.

The term "and/or" as used herein refers to and encompasses any and all possible combinations of one or more of the associated listed items. When used in a list of two or more items, the term "and/or" means that any one of the listed items may be used alone or any combination of two or more of the listed items may be used. For example, if a composition, combination, construction, or the like is described as including (or comprising) components A, B, C, and/or D, the composition may include A alone; B alone; C alone; D alone; a combination comprising A and B; a combination comprising A and C; a combination comprising A and D; a combination comprising B and C; a combination comprising B and D; a combination comprising C and D; a combination comprising A, B and C; a combination comprising A, B and D; a combination comprising A, C and D; a combination comprising B, C and D; or a combination comprising A, B, C and D.

EXAMPLE 1 SEPARATED CULTURE OF MSCS

In accordance with the guidance of the Animal Ethics Committee, mice were sacrificed with excess $CO_2$. Under sterile conditions, the tibia and femur were removed, and the attached muscle and connective tissue were stripped out. Then the metaphysis was further separated to expose the bone marrow cavity. PBS containing 10% by volume of fetal bovine serum was drawn using a 10 mL sterile syringe to repeatedly flush the bone marrow cavity, and was filtered with a 70 μm pore cell strainer, and centrifuged at 500 g for 5 min. After the supernatant was removed, the cell pellet at the bottom was collected, and then resuspend in PBS and centrifuged at 500 g for 5 min again to collect the final cell pellet. The cells were then subjected to flow cytometry sorting with CD34– and CD90+ as sorting criteria, such that bone marrow mesenchymal stem cells (BMMSCs) were separated. Finally, the cells were resuspended in a Dex (–) culture solution, and inoculated to a 10 cm diameter cell culture dish and cultured at 37° C. in 5% $CO_2$. After 24 h, non-adherent cells in the supernatant were removed by aspiration, washed with PBS, and added into the Dex (–) culture solution for further culture. After 1 week, an equal amount of Dex (+) culture solution was added, and after another week, dense primary BMMSCs colonies were observed. The BMMSCs were digested by trypsin incubation at 37° C., and passaged for amplification. Thereafter, the Dex (+) culture solution was changed every 3 days, and subcultured if confluent. The BMMSCs of second passage (P2) were taken for subsequent experiments.

The composition of the Dex (–) culture solution is shown in Table 1, and the composition of Dex (+) culture solution is shown in Table 2:

TABLE 1

Composition of Dex (–) culture solution

| Reagents | Volume | Final concentration |
| --- | --- | --- |
| FBS | 100 mL | 20% |
| Penicillin/Streptomycin | 5 mL | 100 U/mL |

TABLE 1-continued

Composition of Dex (−) culture solution

| Reagents | Volume | Final concentration |
|---|---|---|
| Solution (10,000 U/mL) | | |
| Glutamine (200 mM) | 5 mL | 2 mM |
| 2-ME (55 mM) | 500 μL | 55 μM |
| α-MEM | Add to 500 mL | |

TABLE 2

Formulation of Dex (+) culture solution

| Reagents | Volume | Final concentration |
|---|---|---|
| FBS | 100 mL | 20% |
| Penicillin/Streptomycin Solution (10,000 U/mL) | 5 mL | 100 U/mL |
| Glutamine (200 mM) | 5 mL | 2 mM |
| Dexamethasone Sodium Phosphate ($10^{-4}$M) | 50 μL | $10^{-8}$M |
| 2-ME (55 mM) | 500 μL | 55 μM |
| α-MEM | Add to 500 mL | |

The purity of the separated BMMSCs was assessed by flow cytometry analysis of surface markers. For surface marker identification, P2 BMMSCs were harvested by trypsinization, and then washed once with PBS containing 3% FBS to be resuspended in the PBS at a density of $5 \times 10^5$/mL. Then, 1 μL of PE fluorescent conjugated CD29, CD44, CD90, CD45, and CD34 antibodies were added, with the blank group left. Incubation was carried out for 30 min in the dark at 4° C., followed by washing with PBS for 2 times, and then tests were carried out on the instrument. The test results were as shown in FIG. 1

EXAMPLE 2 PREPARATION OF BMMSCS-DERIVED IEVS

MSCs (bone marrow-derived MSCs) cultured to the second passage in Example 1 was further cultured with the medium (Dex (+) culture solution) in Example 1 until the cells were 80%-90% confluent, then washed twice with PBS, added with a serum-free medium (α-MEM medium) containing 500 nM STS to induce apoptosis, and incubated at 37° C. for 16-24 h. The cell supernatant was collected, and centrifuged at 800 g for 10 min at 4 C. The supernatant was collected and centrifuged at 2000 g for 10 min at 4 C. Then then supernatant was collected and centrifuged again at 16000 g for 30 min at 4 C, and the resulting pellet is IEVs. The pellet was suspended in 500 μl of PBS and centrifuged again at 16000 g for 30 min at 4 C, thereby obtaining the washed IEVs.

Figure 2:
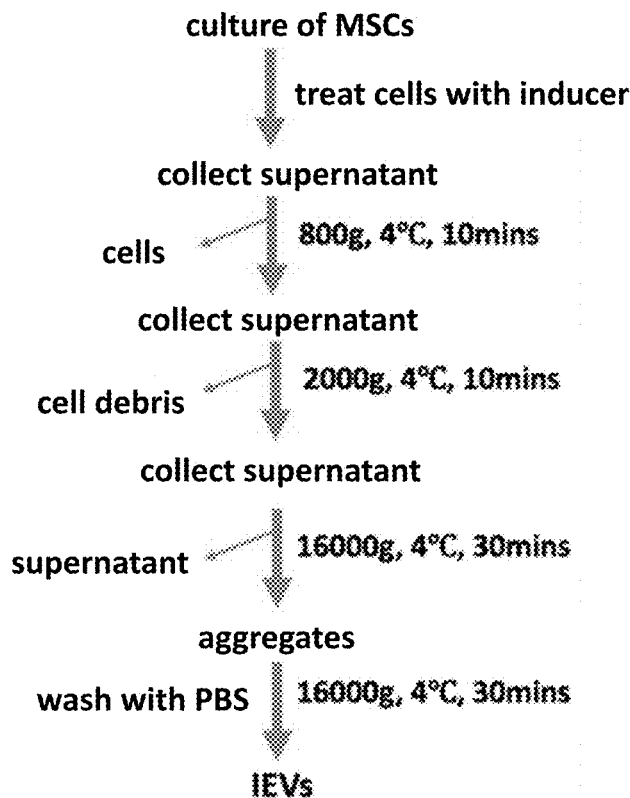
FIG. 2 shows a technical scheme for preparing IEVs according to Example 2.

The preparation route is shown in FIG. 2.

Comparative Example 1 Separation and Extraction of Exosomes from the Same MSCs Source The MSCs (bone marrow-derived MSCs, BMMSCs) cultured to the second passage in Example 1 was further cultured with the medium in Example 1 until the cells were 80%-90% confluent, then washed twice with PBS, added with a serum-free medium, and incubated at 37° C. for 48 h, and the cell supernatant was collected for separation and extraction of exosomes.

The extraction steps include: centrifuge at 800 g for 10 min—collect supernatant—centrifuge at 2000 g for 10 min—collect supernatant—centrifuge at 16000 g for 30 min—collect supernatant—centrifuge at 120000 g for 90 min—remove supernatant, and resuspend pellet in sterile PBS—centrifuge again at 120000 g for 90 min, remove supernatant, collect exosomes, and resuspend in sterile PBS.

Figure 3:
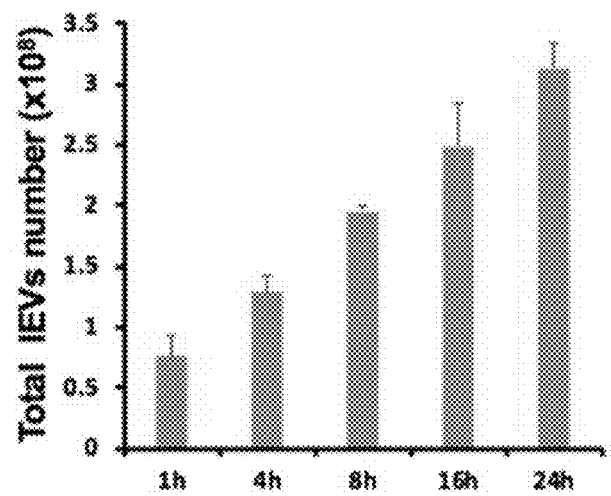
FIG. 3 shows the statistics on the count of IEVs produced by MSCs ($10^6$ MSCs) analyzed by flow cytometry.

EXAMPLE 3 ANALYSIS OF MSCS (1) Quantitative and Membrane Protein Analysis of IEVs The quantitative analysis of IEVs obtained in Example 2 was performed using flow cytometry, and the time points for measurement were 1 h, 4 h, 8 h, 16 h and 24 h. The results showed that $10^6$ MSCs could produce $0.76 \times 10^8$, $1.29 \times 10^8$, $1.95 \times 10^8$, $2.48 \times 10^8$ and $3.14 \times 10^8$ IEVs after induction to 1 h, 4 h, 8 h, 16 h and 24 h, respectively. It can be seen that a single MSC could produce 300 IEVs after induction to 24h (FIG. 3).

Figure 4A:
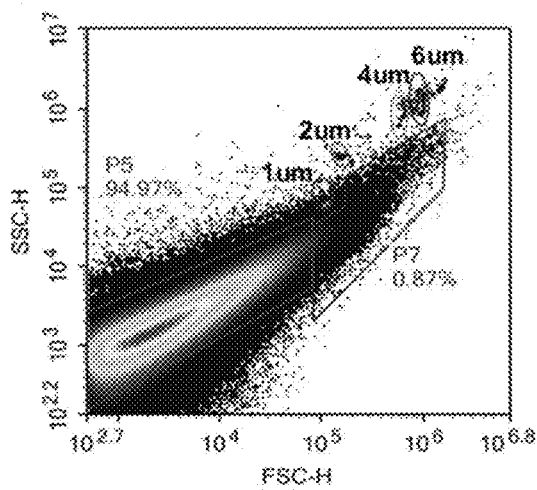
FIGS. 4A-4F show diameter measurements of IEVs particles.

In addition, the particle diameter distribution of IEVs found by flow cytometry was concentrated within less than 1 μm, accounting for 94.97% (FIG. 4A).

Figure 4B:
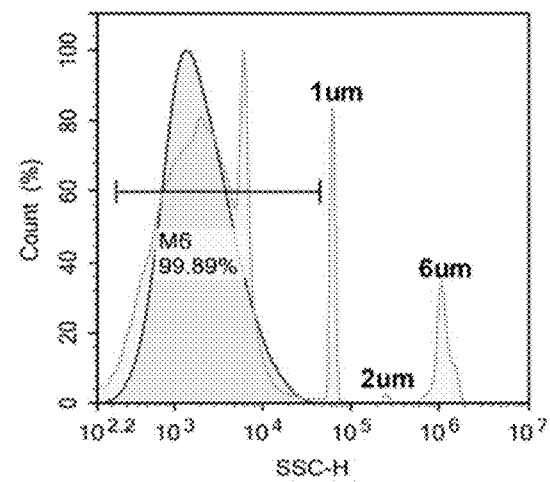

The results of Side Scatter (SSC) analysis also showed that the scattered light intensity of IEVs was concentrated in the range of less than 1 μm (FIG. 4B).

Figure 4C:
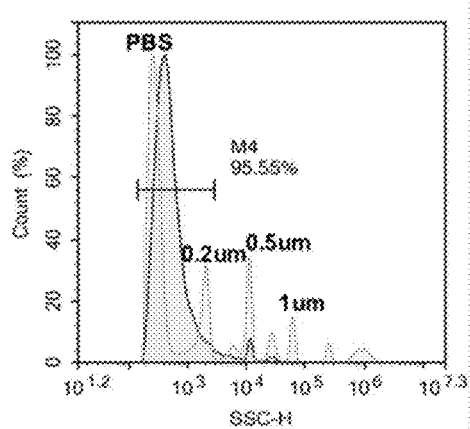

Further, the scattered light intensity of IEVs was analyzed by standardized small particle microspheres (0.2 μm, 0.5 μm, 1 μm) produced by Bangs Laboratories, and the results showed that the particle diameters of IEVs were all below 0.2 μm (FIG. 4C).

Figure 4D:
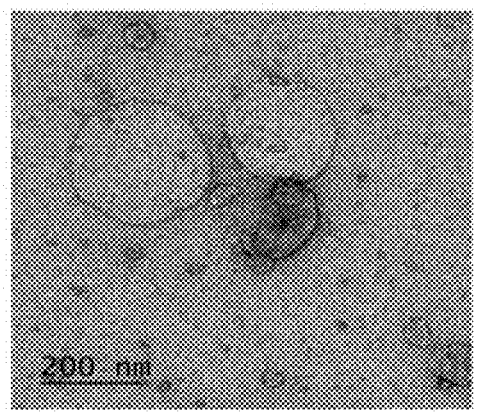

Transmission electron microscopy (TEM) showed similar results as flow cytometry, with most vesicles at and below 200 at 200 nm in diameter (FIG. 4D).

Figure 4E:
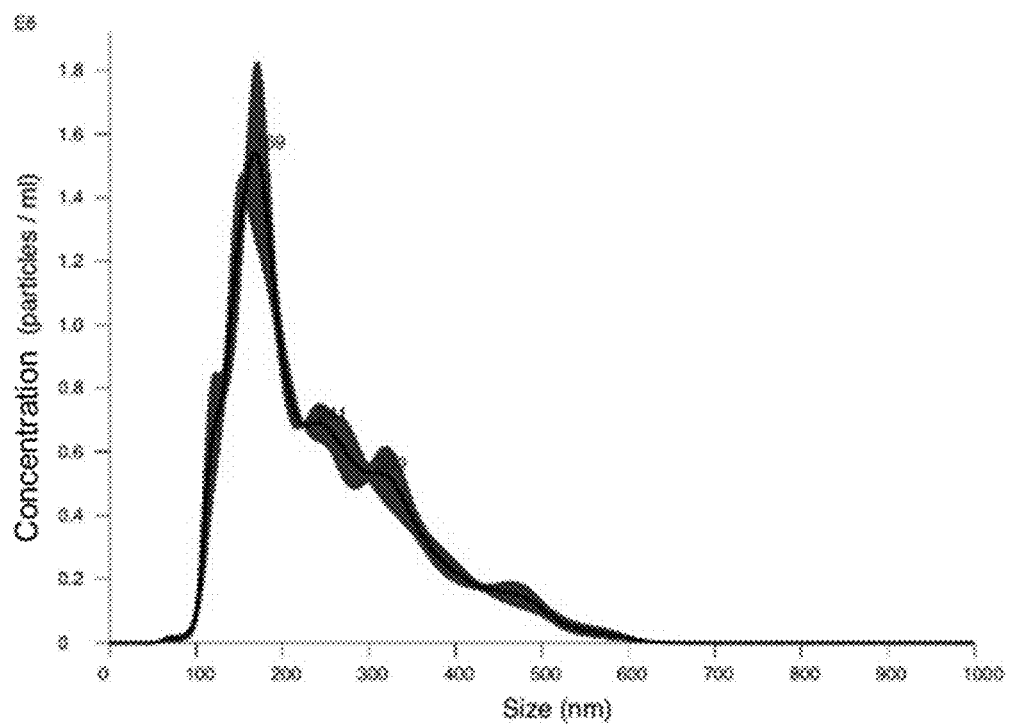

Nanoparticle Tracking Analysis (NTA) was consistent with TEM observations, with IEVs particles averaging 169 nm in diameter (FIG. 4E).

Figure 4F:
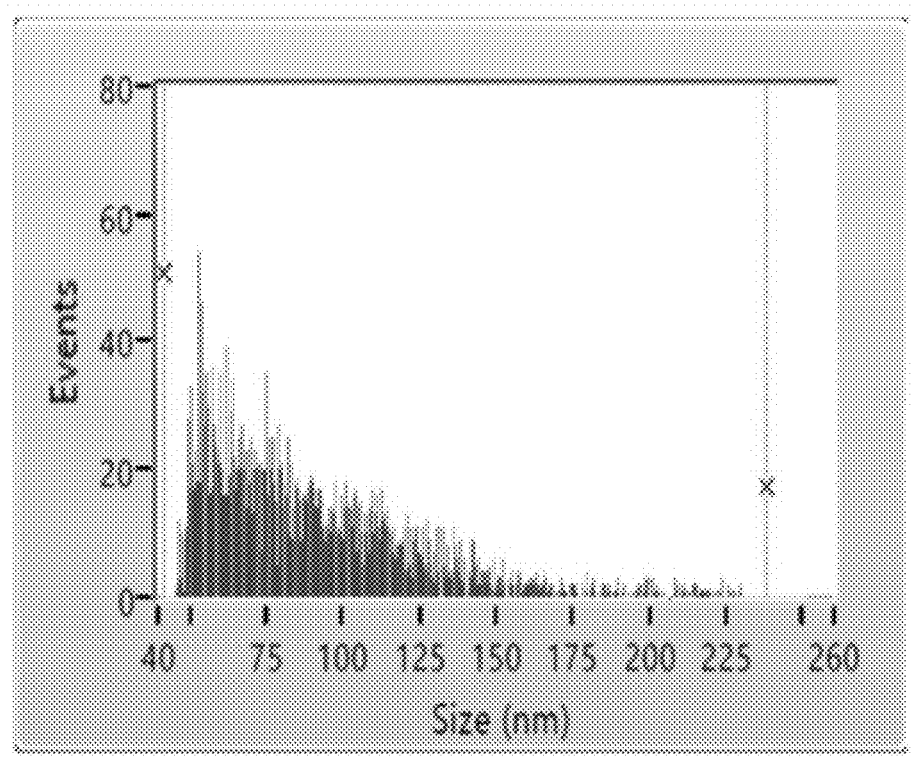
Figure 5A:
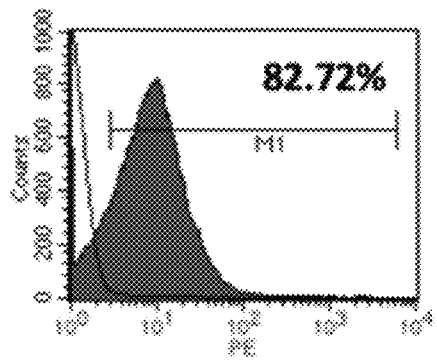
FIGS. 5A-5K show the results of surface membrane protein analysis of IEVs by flow cytometry.
Figure 5B:
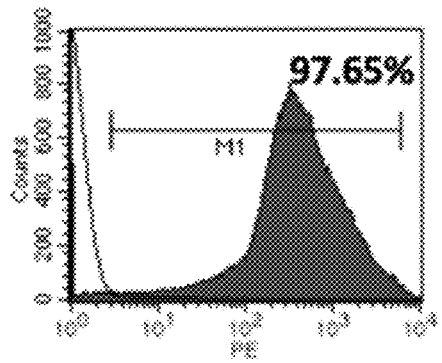
Figure 5C:
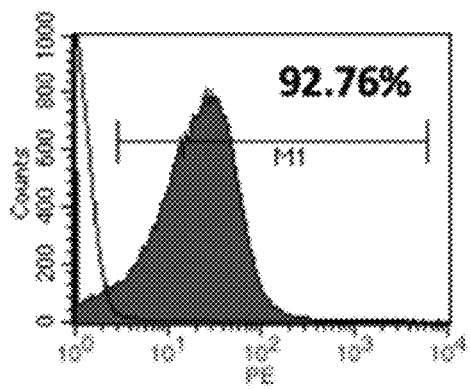
Figure 5D:
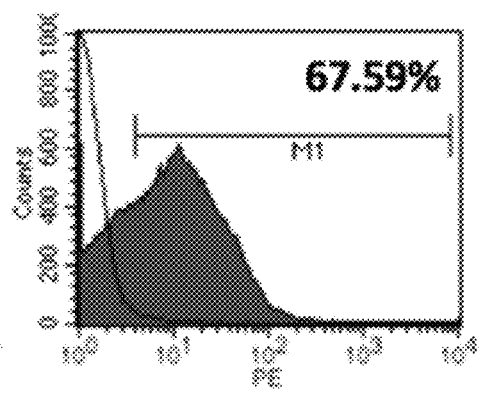
Figure 5E:
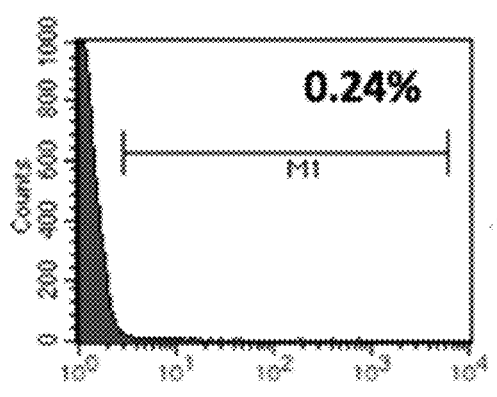
Figure 5F:
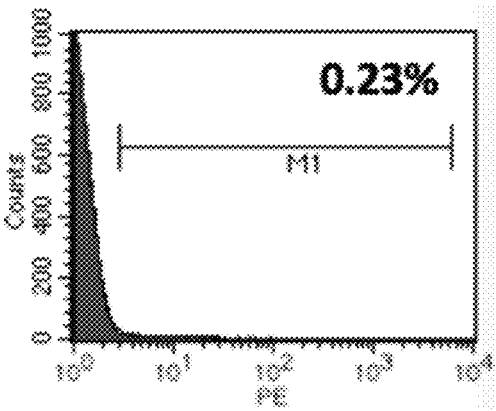
Figure 5G:
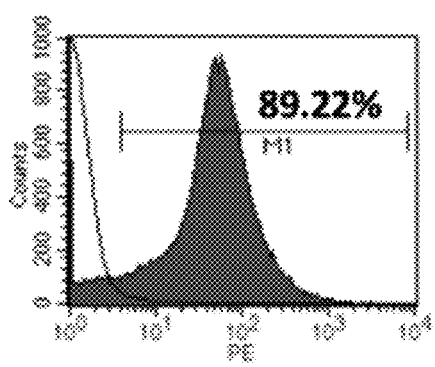
Figure 5H:
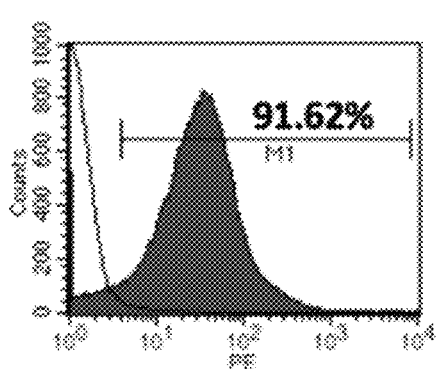
Figure 5I:
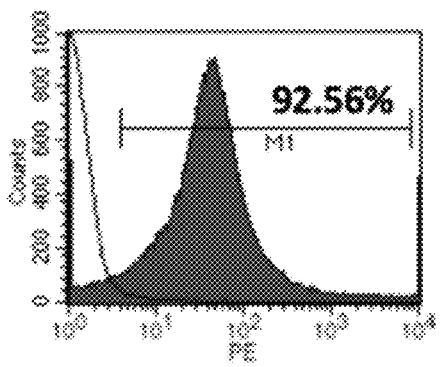
Figure 5J:
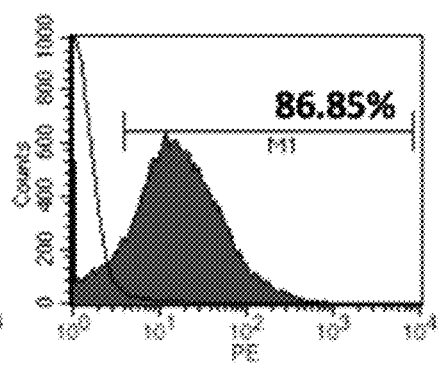
Figure 5K:
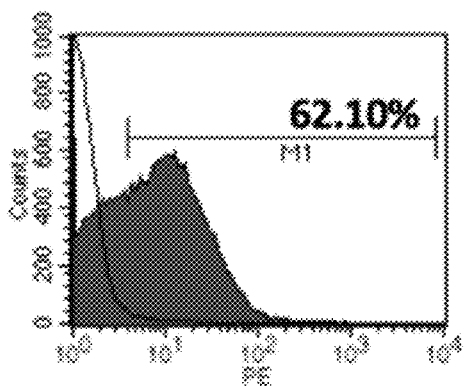

Particle size measurements at the single-vesicle level using a state-of-the-art nano-flow cytometry technology also showed that the average particle diameter of IEVs was at 100.63 nm (FIG. 4F).

The surface membrane proteins of the IEVs extracted in Example 3 were analyzed by flow cytometry, and the results showed that the IEVs derived from MSCs expressed surface proteins similar to MSCs, i.e., CD29, CD44, CD73, CD166 positive, and CD34, CD45 negative. At the same time, IEVs could express the ubiquitous surface proteins CD9, CD63, CD81 and C1q of extracellular vesicles (FIG. 5A-5K).

(2) Content Analysis of IEVs

Figure 6A:
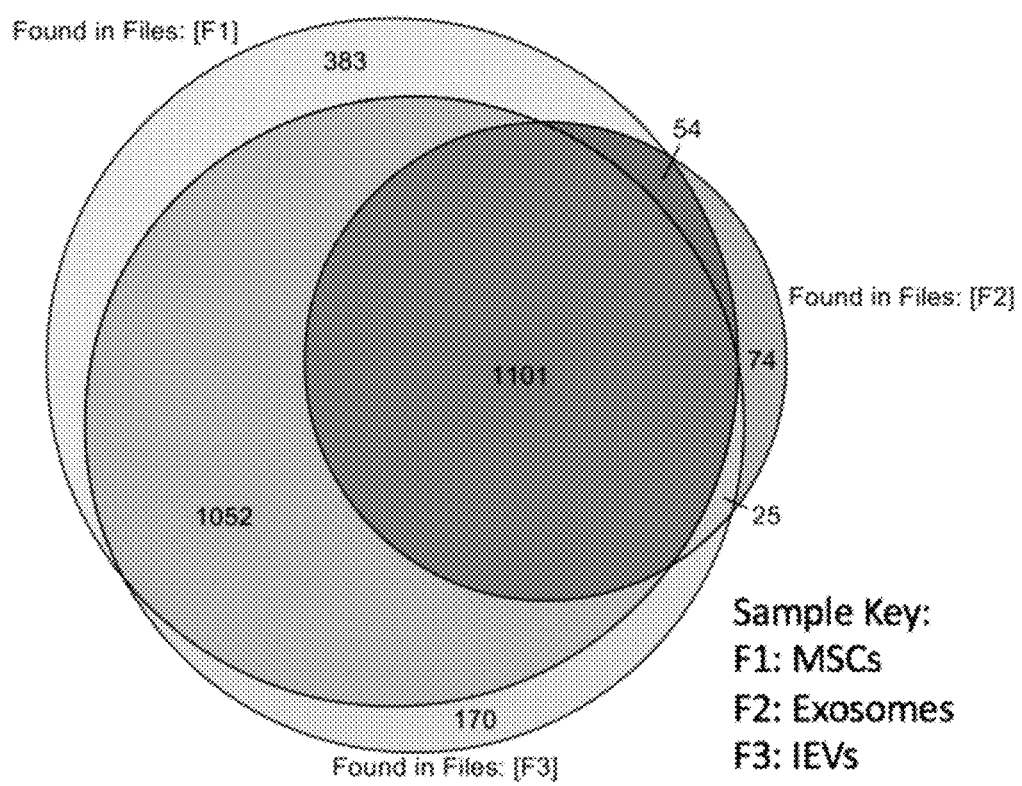
FIGS. 6A-6D show the content analysis of IEVs.
Figure 6B:
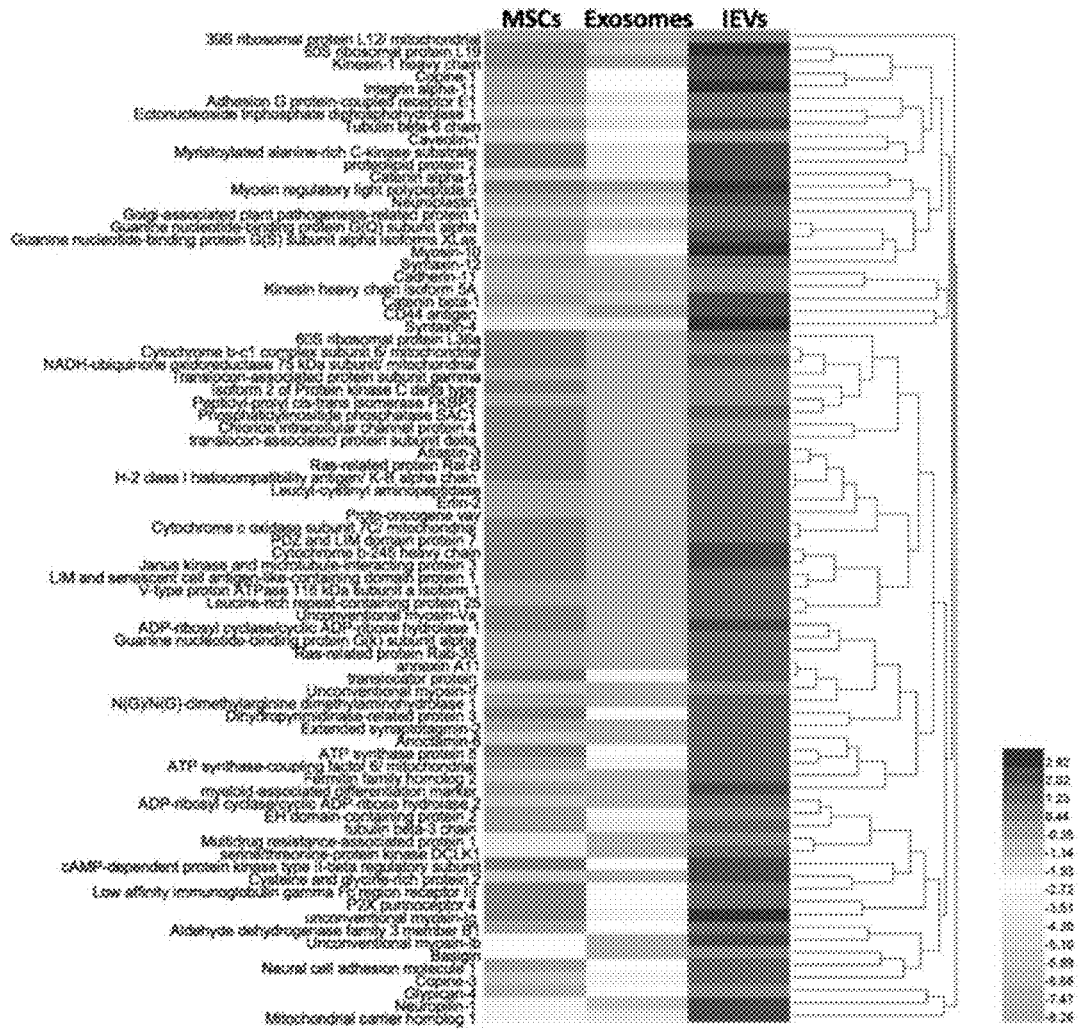
Figure 6C:
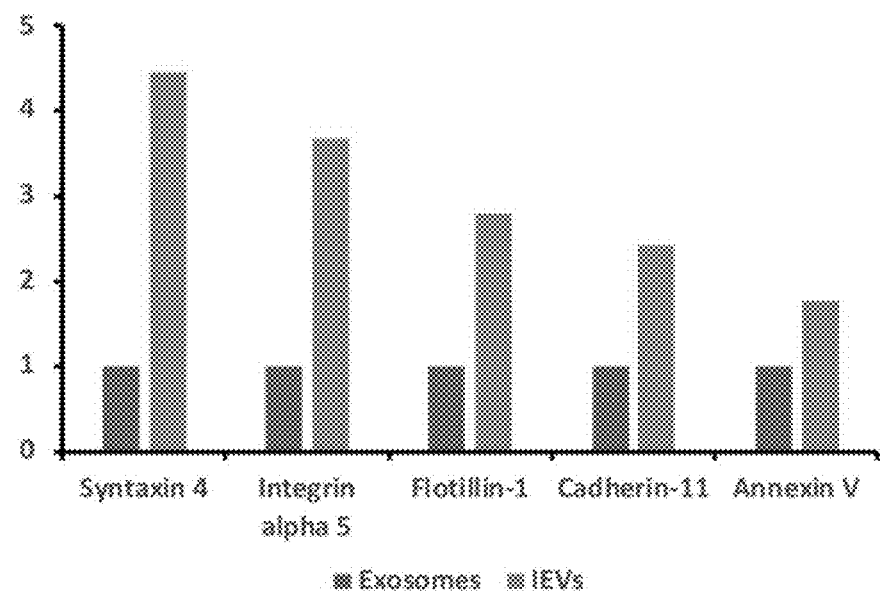
Figure 6D:
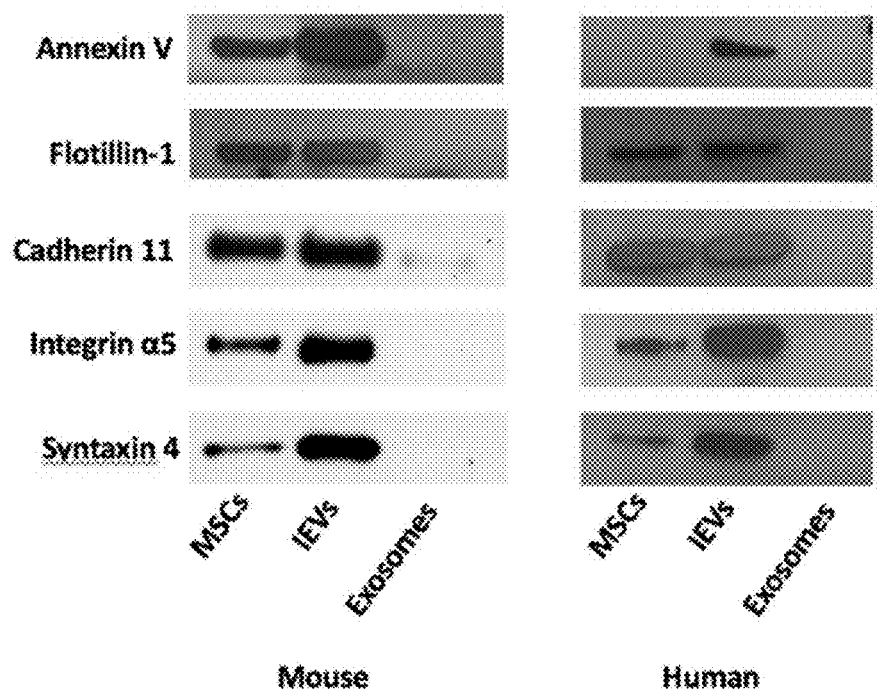

Proteomic quantification of MSCs, MSCs-Exosomes (extracted in Comparative Example 1), and MSCs-IEVs (obtained in Example 2) was performed using the protein DIA quantification technique. The results showed that the protein content expression of MSCs-Exosomes and MSCs-IEVs had a high overlap with that of the parent cells, and 170 proteins were specifically highly expressed in IEVs (FIG. 6A). Through bioinformatics analysis, IEVs-specific and highly expressed proteins were screened, and a heat map was drawn (FIG. 6B). By further combining with GO enrichment analysis results of differential proteins, it is confirmed that IEVs can specifically express Annexin V, Flotillin-1, Cadherin 11, Integrin alpha 5, and Syntaxin 4 molecules at high levels. Compared with Exosomes derived from the same MSCs, the expression levels of the 5 characteristic molecules of IEVs are all significantly up-regulated, specifically: the expression levels of the markers Annexin V, Flotillin-1, Cadherin 11, Integrin alpha 5, and Syntaxin 4 in IEVs are 1.76 fold, 2.81 fold, 2.41 fold, 3.68 fold and 4.45 fold, respectively, of that in exosomes. Finally, it was verified again with the Western Blot technology, and the results were consistent with the results of the DIA quantitative analysis (FIG. 6D).

MSCs-Exosomes: exosomes derived from BMMSCs.
MSCs-IEVs: IEVs derived from BMMSCs.

The MSCs in the content analysis and the MSCs for extraction of the exosomes and IEVs are from the same cell strain.

EXAMPLE 4 EXCRETION OF IEVS THROUGH THE SKIN AND HAIR $4 \times 10^6$ IEVs prepared in Example 2 was labeled with DIR, and resuspended in 200 μL of PBS, and then systemically injected into nude mice BALB/c-nu/nu through the tail veins. The distribution of IEVs on the skin surface was observed after 1, 3 and 7 days using a living body imaging instrument, and the results were as shown in FIGS. 7A-7C.

Figure 7A:
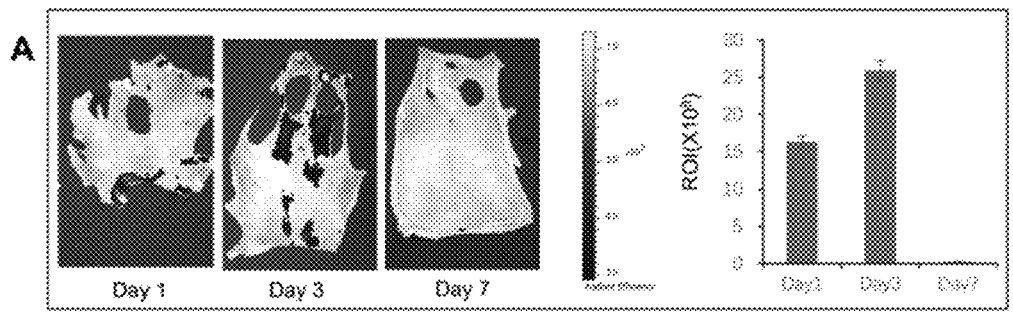
FIG. 7A shows dynamic metabolism of IEVs on the skin surface according to Example 3.
Figure 7B:
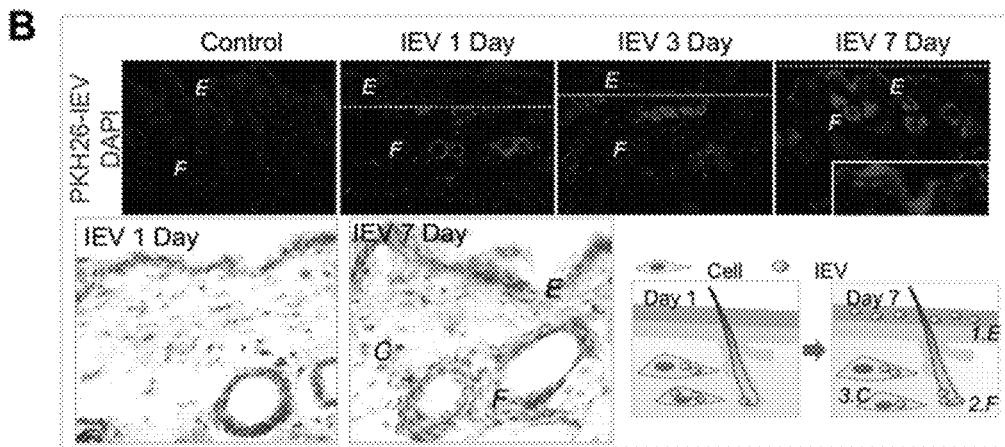
FIG. 7B shows the gradual migration of IEVs from the subcutaneous tissue to the dermis and epidermis over time.
Figure 7C:
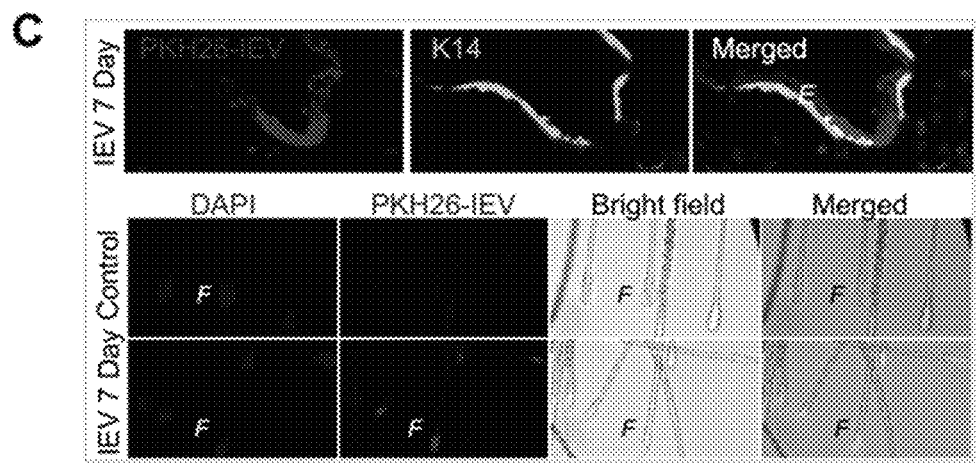
FIG. 7C shows the presence of PKH26-IEVs in hair follicles found in hairs removed from the surface of mice on Day 7.

FIG. 7A showed that IEVs can reach the skin surface with the largest amount on Day 3, and substantially disappear on Day 7, indicating a dynamic metabolic process of IEVs on the skin surface (FIG. 7A) Immunofluorescence results showed that after systemic injection of C57 mice with PKH26-IEV, it gradually moved from the subcutaneous tissue to the dermis and epidermis over time. Large amounts of IEVs were observed on the stratum corneum at the skin surface on Day 7, suggesting that the systemically injected IEVs could be excreted as the stratum corneum sloughs off (FIG. 7B). Meanwhile, the presence of PKH26-IEV in hair follicles was found in hairs extracted from the surface of mice on Day 7, indicating that the systemically injected IEVs were also metabolized as hairs fell off (FIG. 7C).

Figure 8A:
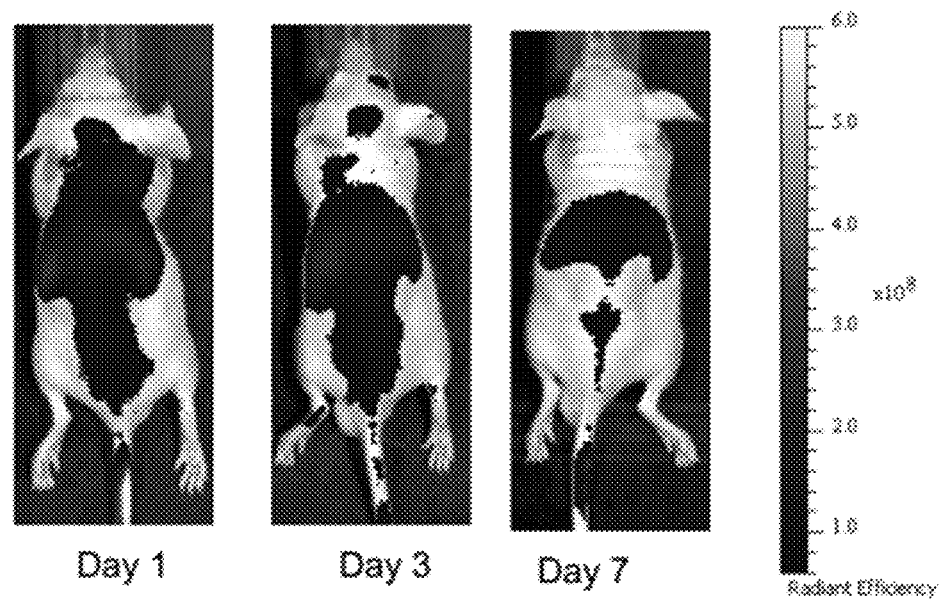
FIG. 8A shows the distribution of IEVs throughout the body of mice on Day 1, 3 and 7 as measured by in vivo imaging.
Figure 8B:
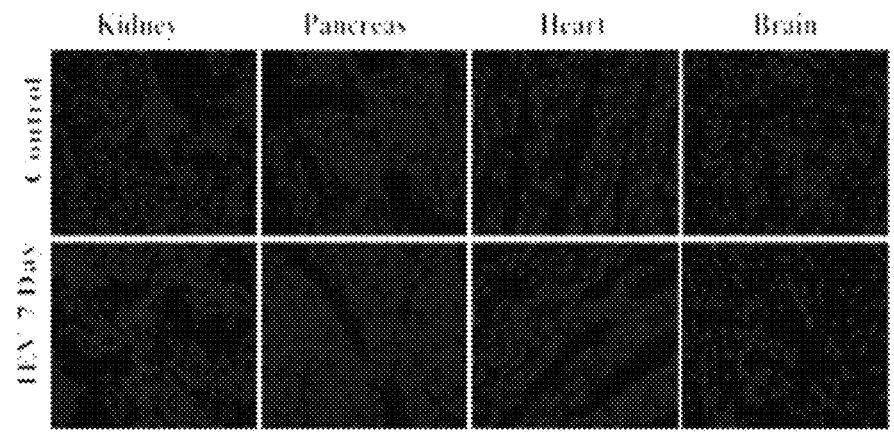
FIG. 8B shows the distribution of IEVs in various organs of mice on Day 7 as compared to a control group.
Figure 8C:
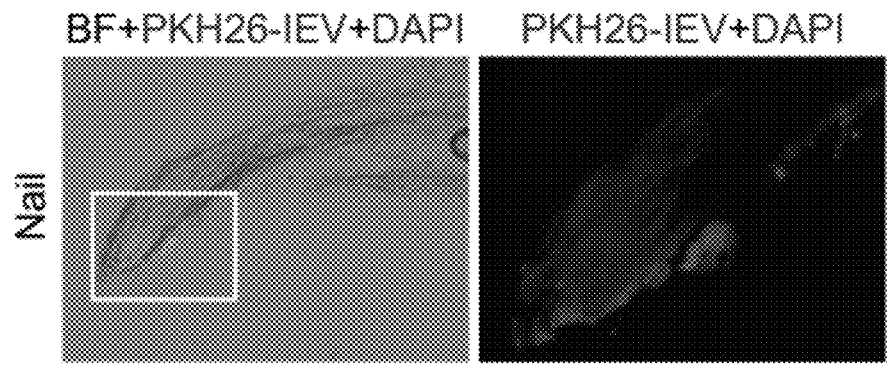
FIG. 8C shows the metabolism of IEVs in the nails and incisors of mice on Day 3.

In addition, both in vivo imaging data and immunofluorescence results showed that IEVs were not distributed in heart, kidney and brain, but distributed in nails, further demonstrating that IEVs can be excreted in vitro with metabolism (FIGS. 8A-8C).

This example demonstrates that IEVs can be excreted through the skin and hair, demonstrating the safety of injecting or increasing the level IEVs in the body.

EXAMPLE 5 HAIR REGROWTH PROMOTING EFFECT OF IEVS

Figure 9A:
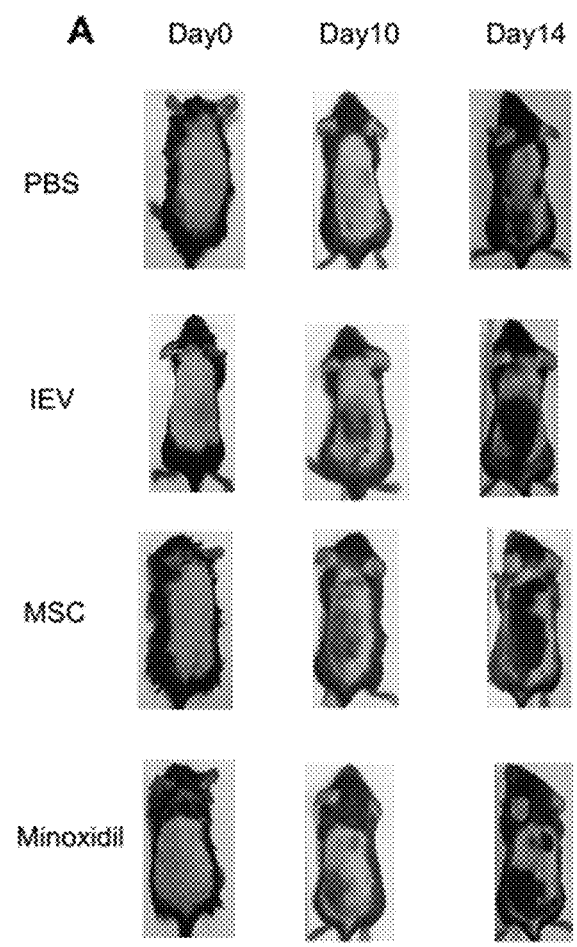
FIG. 9A shows the back hair regrowth on Day 0, 10, and 14 in mice treated differently as described in Example 4.
Figure 9B:
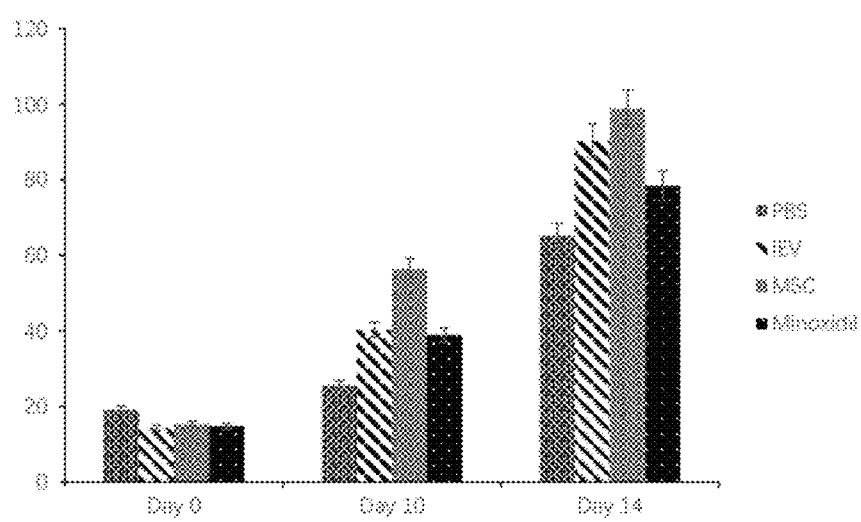
FIG. 9B shows a statistical analysis of the area of back hair regrowth on Day 0, 10, and 14 in mice treated differently as described in Example 4.

Seven weeks old female C57 mice (telogen) were depilated with subcutaneous injections of PBS, IEVs, MSCs and 2% Minoxidil. Comparing the hair regrowth area on the backs of the mice on Day 10 and Day 14, the results showed that both IEVs and MSCs had significant hair regrowth promoting effect as compared with the control group, and both IEVs and MSCs had more significant hair regrowth promoting effect on Day 14 than the traditional anti-alopecia drug minoxidil (FIGS. 9A-9B).

EXAMPLE 6 HAIR REGROWTH PROMOTING EFFECT OF IEVS INTRODUCED BY MICRONEEDLE PATCH

A 1300-needle microneedle patch was used to introduce human umbilical cord mesenchymal stem cells (UCMSCs)-derived IEVs into the back of C57 mice.

The UCMSCs-derived IEVs were obtained in the following way:

The cells used were umbilical cord mesenchymal stem cells (UCMSCs) provided by Nanjing Taisheng Biotechnology Co. Ltd. After the obtained UCMSCs were treated with STS (500 nm) for 10 hours to induce apoptosis, IEVs were extracted according to the following procedures:

1. After the induction was completed, the induced cells were taken from the incubator, and a pipette was used to blow and beat the bottom and walls of the dish. After mixing well, the suspension was aspirated out and collected in a sterile centrifuge tube with a corresponding number, and centrifuged for 10 min at a rotation speed of 800 g under the temperature of 4° C.

2. After centrifugation was completed, the supernatant in the centrifuge tube was sucked out and collected in a newly prepared sterile centrifuge tube with a corresponding number for secondary centrifugation and purification. The pellet in the tube was used for apoptosis rate detection.

3. At the same time, the supernatant collected after the centrifugation is further centrifuged for 10 min at a rotation speed of 2000 g at a temperature of 4° C.

4. After the centrifugation was completed, the supernatant was collected, and the pellet discarded, with the whole process under observation.

5. The supernatants was sucked into the new sterile tube with the corresponding number for subsequent use.

6. After the second centrifugation, the supernatant collected in the centrifuge tube is further centrifuged for 30 min at a rotation speed of 16000 g and at a temperature of 4° C.

7. After centrifugation, the pellet was collected, and the supernatant was discarded, with the whole process under observation.

8. Normal saline was prepared, and after the completion of centrifugation, the supernatant was discarded, and the normal saline was added into the centrifuge tube in proper amounts, followed by blowing, beating, suspending and washing until until the liquid phase is uniform by visual observation. The centrifugation was continued for 30 min at 16000 g at 4° C.

9. After the centrifugation was completed, the supernatant was discarded, and the normal saline was added into the centrifuge tube in an appropriate amount for mixing with and suspending the pellet.

Aseptically, the skin on the back of C57 mice was fixed and shaved with a microneedle patch using an adhesive tape, and 1 hour later, the surface of the test skin was coated with IEVs ($4 \times 10^6$ umbilical cord-derived mesenchymal stem cells).

The design of each treatment group is shown in Table 3.

TABLE 3

| Group | Carrier |
| --- | --- |
| 1 | Control group |
| 2 | Subcutaneous injection of IEVs |
| 3 | 1300-needle microneedle introduction of IEVs: |

Figure 10:
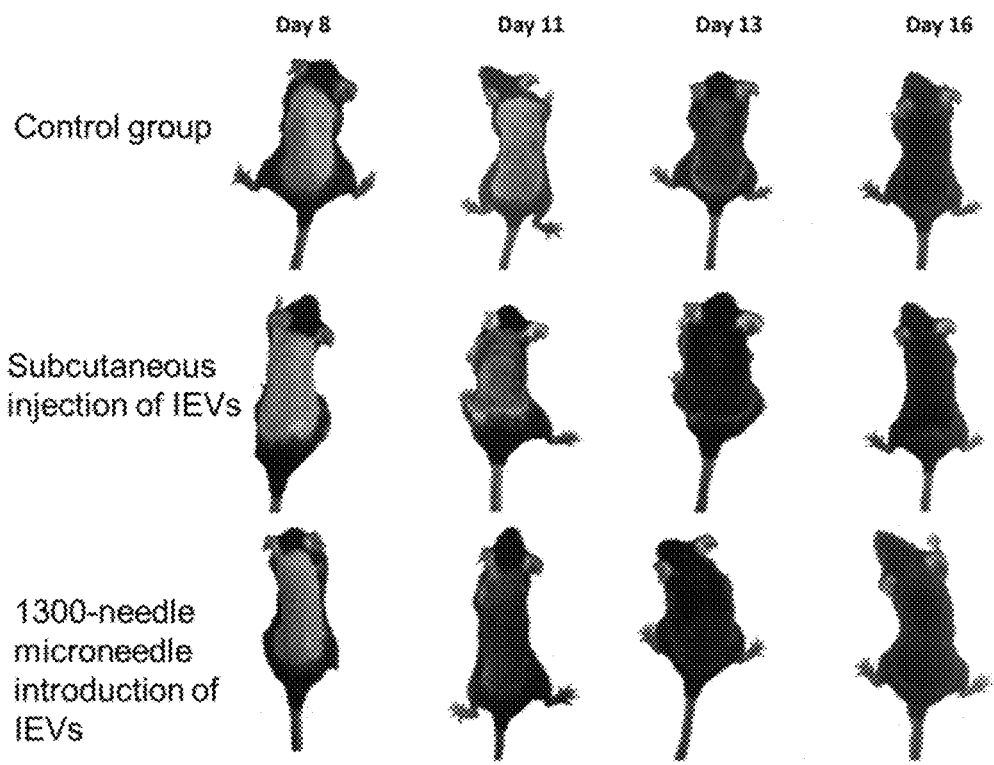
FIG. 10 shows the back hair regrowth on Day 0, 11, 13, and 16 in mice treated differently as described in Example 6.

As shown in FIG. 10, the introduction of IEVs with the 1300-needle microneedle patch had a good hair regrowth promoting effect.

EXAMPLE 7 SIGNIFICANT PROMOTING EFFECT OF RAPAMYCIN, METFORMIN, DASATINIB AND RESVERATROL COMBINED WITH IEVS ON EXCRETION OF IEVS ON THE SKIN SURFACE AND HAIR REGROWTH RATE, AND COMPARISONS

Figure 11:
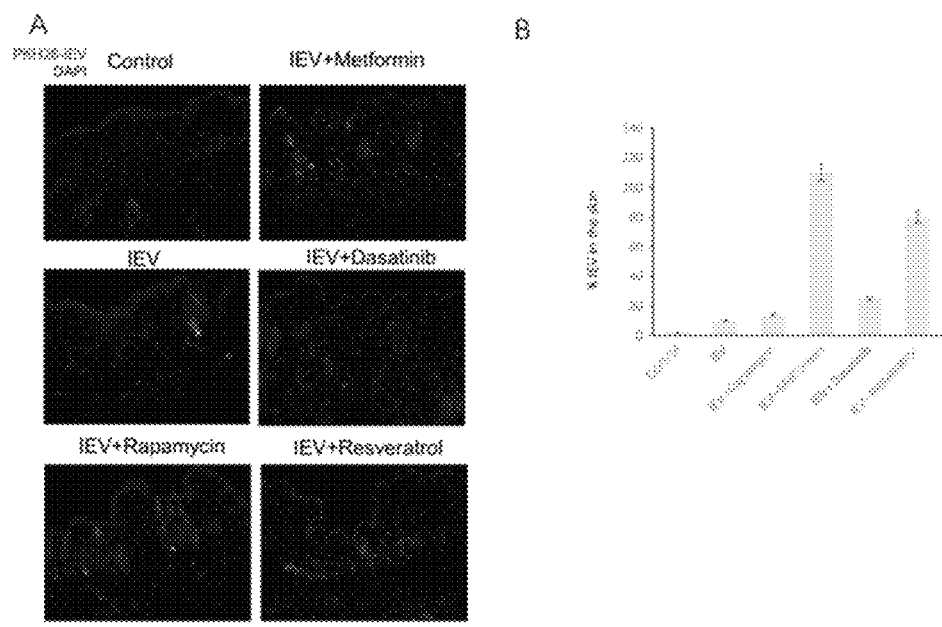
FIG. 11 shows the distribution of IEVs on the skin surface after 7 days for IEVs combined with different drugs as described in Example 5.

After systemic injection of PKH26-IEV in C57 mice, rapamycin (5 mg/kg), metformin (100 mg/kg), dadatinib (5 mg/kg) and resveratrol (10 mg/kg) were intraperitoneally injected for 7 days, respectively. The immunofluorescence results showed that metformin could significantly increase the excretion of IEVs in skin tissues, followed by resveratrol. Rapamycin and dasatinib had no obvious enhancement effect (FIG. 11).

Figure 12:
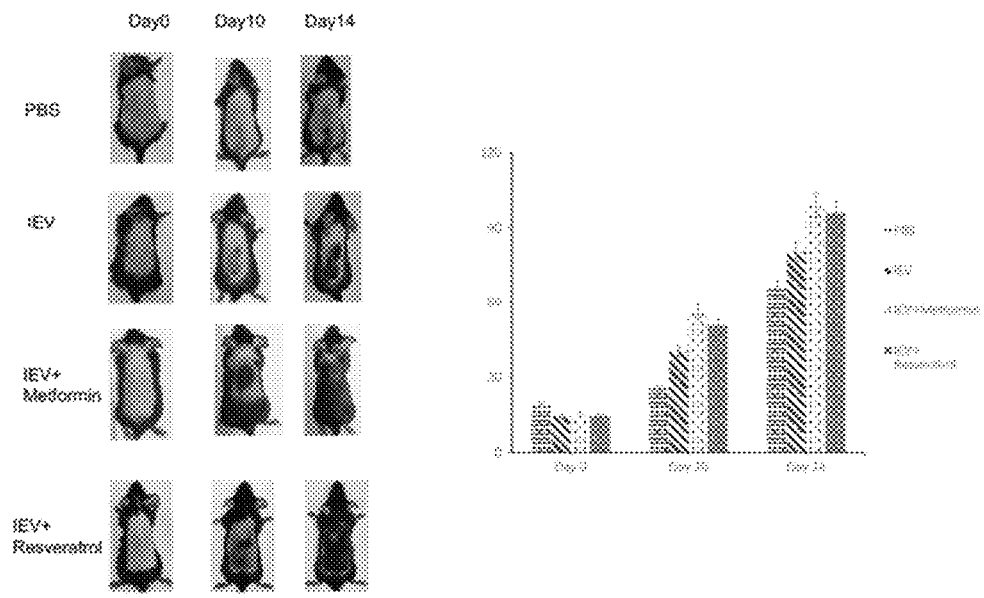
FIG. 12 the hair regrowth promoting effects of IEVs combined with different drugs as described in Example 5.

The results of hair regrowth in mice showed that the IEVs significantly promoted hair regrowth, while the combination of anti-aging substances, such as metformin or resveratrol, promoted the promotion effects of hair regrowth by IEVs (FIG. 12).

This example shows that the combination of metformin or resveratrol with IEVs can effectively promote the excretion of IEVs in the skin, shorten the time of IEVs in the body and improve the safety of IEVs.

This example also shows that metformin or resveratrol in combination with IEVs can promote hair regrowth, suggesting the possibility of using the combination of an anti-aging substance and IEVs as a hair regrowth promoting drug.

EXAMPLE 8 REGULATION EFFECT OF WNT SIGNALING PATHWAYS ON METABOLISM OF IEVS IN THE SKIN

The Wnt pathway is a classical signaling pathway in cell biology. It keeps cells in a state similar to stem cells, helping them to generate new cells. The Wnt signaling pathway plays an important role in skin self-renewal.

Wnt agonist Licl was dissolved in PBS at 10 mg/kg, and injected intraperitoneally for 3 days; the Wnt inhibitor XAV939 was dissolved at 1 mg/kg in 10% DMSO in normal saline, and injected intraperitoneally for 3 consecutive days.

Figure 13A:
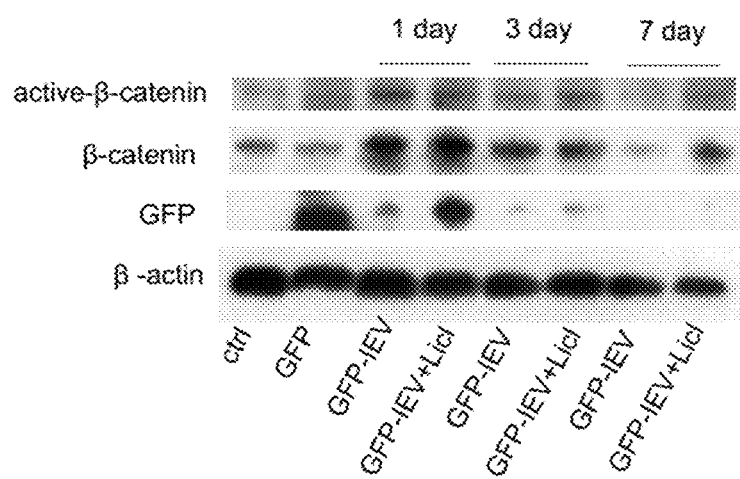
FIG. 13A shows the Western Blot results of Example 6 after administration of the Wnt agonist Licl.
Figure 13B:
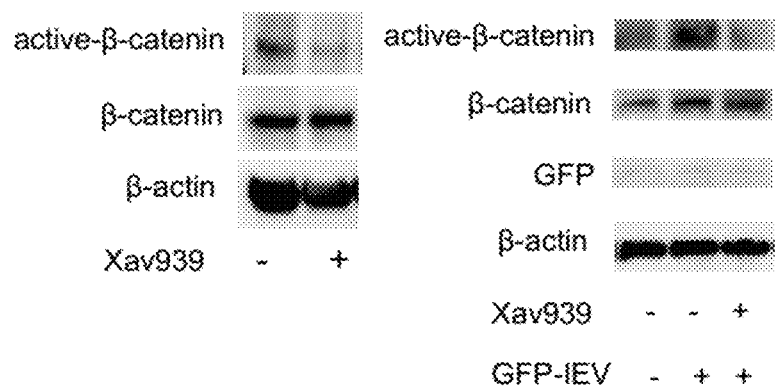
FIG. 13B shows the Western Blot results of Example 6 after administration of the Wnt inhibitor XAV939.
Figure 13C:
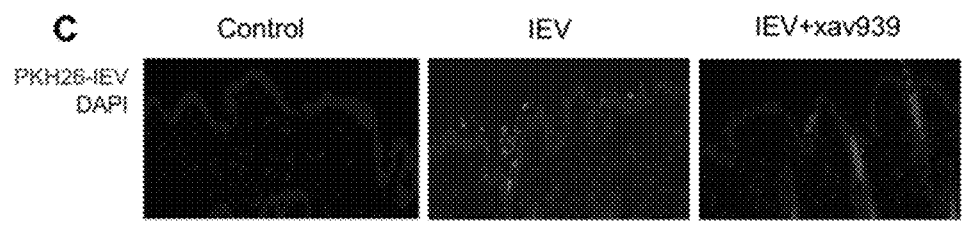
FIG. 13C shows the immunofluorescence results of Example 6 in the presence of XAV939.
Figure 13D:
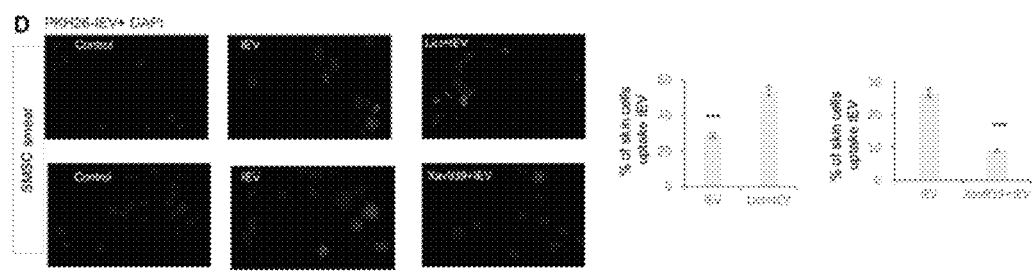
FIG. 13D shows the cell smear results for various treatments as described in Example 6.
Figure 13E:
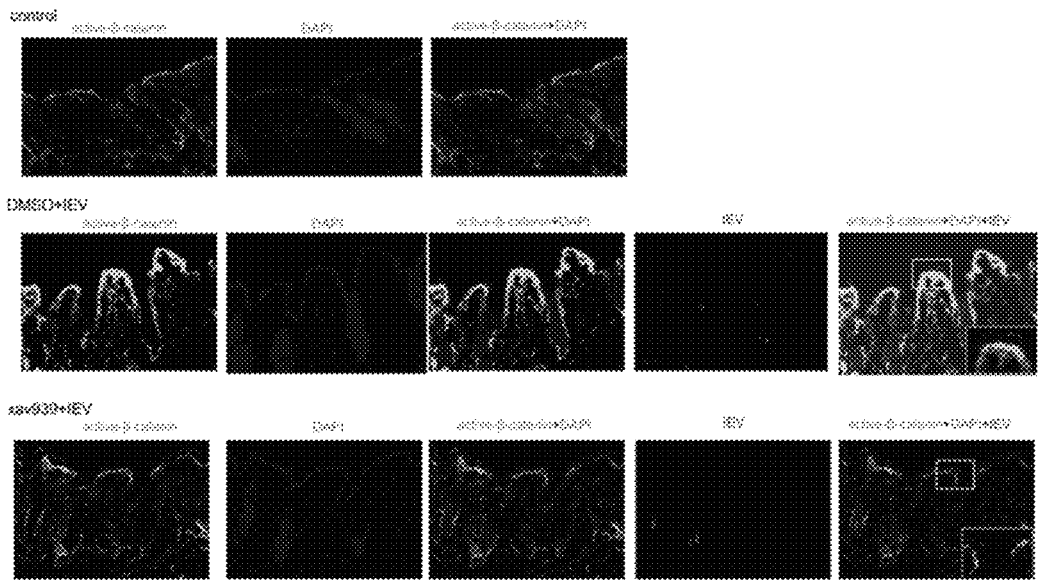
FIG. 13E shows the immunofluorescence results of excretion of IEVs in the epidermis after various treatments as described in Example 6.

The Western Blot results show a significant increase in skin excretion of IEVs with the Wnt agonist Licl and a significant decrease in skin excretion of IEVs with the Wnt inhibitor XAV939 (FIGS. 13A-B) Immunofluorescence results also demonstrated that subcutaneous injection of PKH26-IEV under the influence of XAV939 resulted in greatly reduced excretion through the skin surface (FIG. 13C). Meanwhile, cell smear results showed that the uptake of IEVs by skin mesenchymal stem cells was affected by Licl and XAV939 (FIG. 13D). More importantly, immunofluorescence results demonstrated that the injection of IEVs greatly enhanced the intensity of active-β-catenin in the skin, suggesting that IEVs stimulate the activation of Wnt signaling pathways in the skin, that the XAV939 inhibitor attenuated this activation process, and that the change in the intensity of active-β-catenin was consistent with the change in the amount of IEVs excreted in the epidermal layer (FIG. 13E).

Figures 14A, 14B:
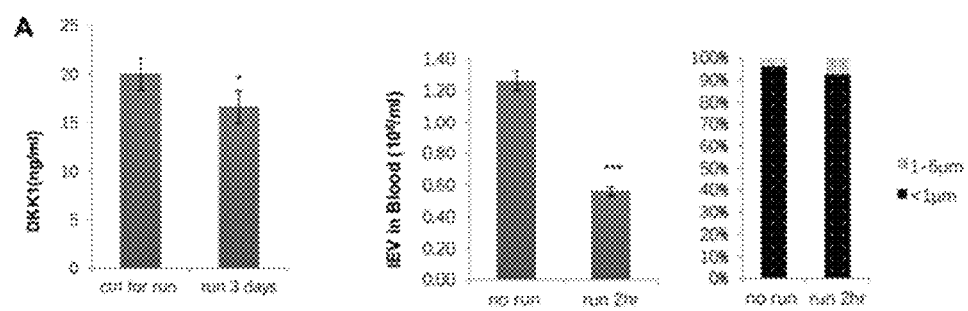
FIG. 14A shows the level of DKK1 in the post-exercise cycle.
FIG. 14B shows the count of IEVs in blood with or without exercise and flow cytometry results.

Exercise has been shown to have a regulatory effect on the Wnt signaling pathways. ELISA results showed a significant decrease in DKK1 levels in the circulation after exercise (FIG. 14A), indicating that exercise could activate the Wnt signaling pathways in vivo.

Figure 14C:
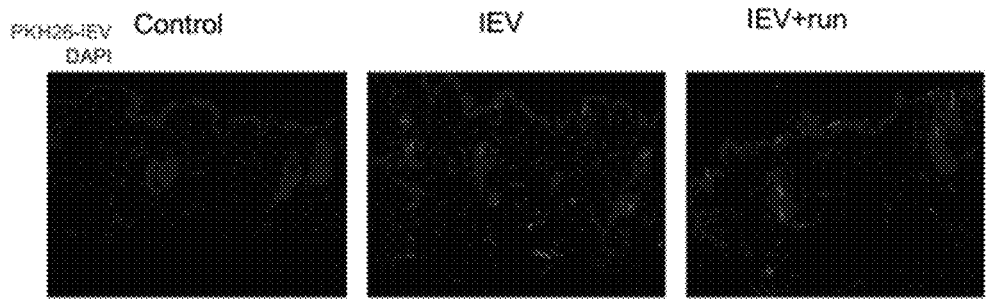
FIG. 14C shows the immunofluorescence results of the output of IEVs excreted on the skin surface after exercise.
Figure 14D:
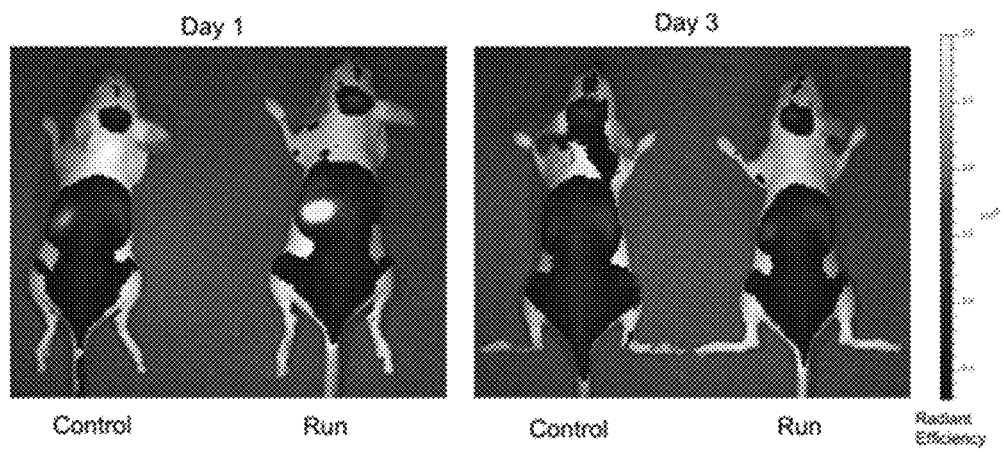
FIG. 14D shows the distribution of IEVs throughout the body of mice after 1 or 3 days of exercise as measured by in vivo imaging.
Figure 14E:
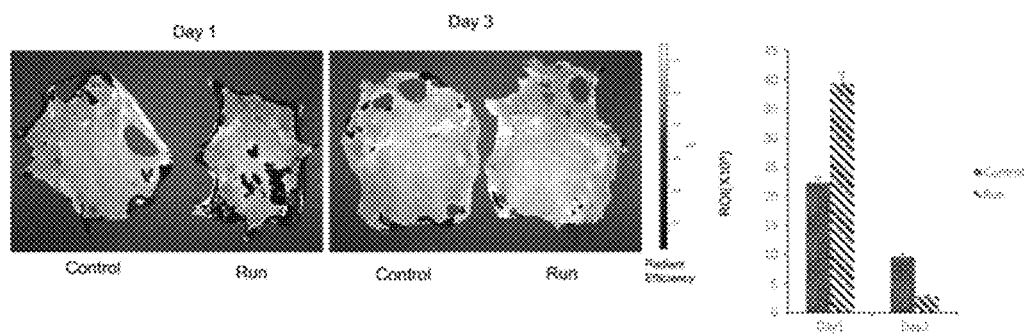
FIG. 14E shows the distribution of IEVs on the skin of mice after 1 or 3 days of exercise as measured by in vivo imaging.
Figure 14F:
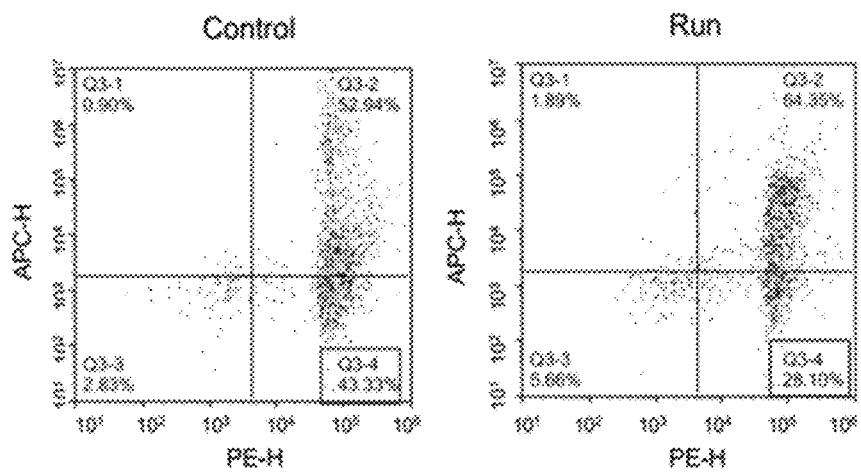
FIG. 14F shows the flow cytometry results of IEVs in vivo (blood) after 7 days of exercise.

Flow cytometry results showed a large decrease in physiological IEVs in mice after exercise (FIG. 14B) Immunofluorescence results showed an increase in the excretion of PKH26-IEV on the skin surface after exercise (FIG. 14C). In vivo imaging results showed a greatly enhanced distribution of IEVs in the body and skin after 1 day of exercise and a decrease compared with the control group after 3 days of exercise (FIGS. 14D-E). The count of PKH-67-labeled IEVs in the body after exercise was measured by flow cytometry, and the results showed that PKH67-IEV was greatly reduced in the blood after 7 days of exercise as compared to the control group (FIG. 14F). These data suggest that exercise may activate the Wnt signaling pathways, facilitating IEV excretion through the skin.

EXAMPLE 9 WOUND HEALING PROMOTING EFFECTS OF IEVS

Figure 15A:
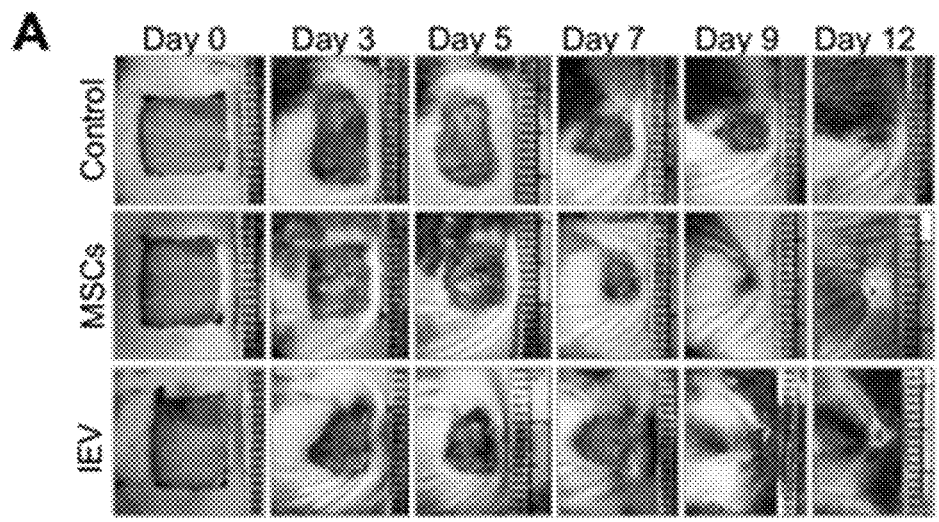
FIG. 15A shows the wound healing promoting effects of IEVs and MSCs treatment as described in Example 7.
Figure 15B:
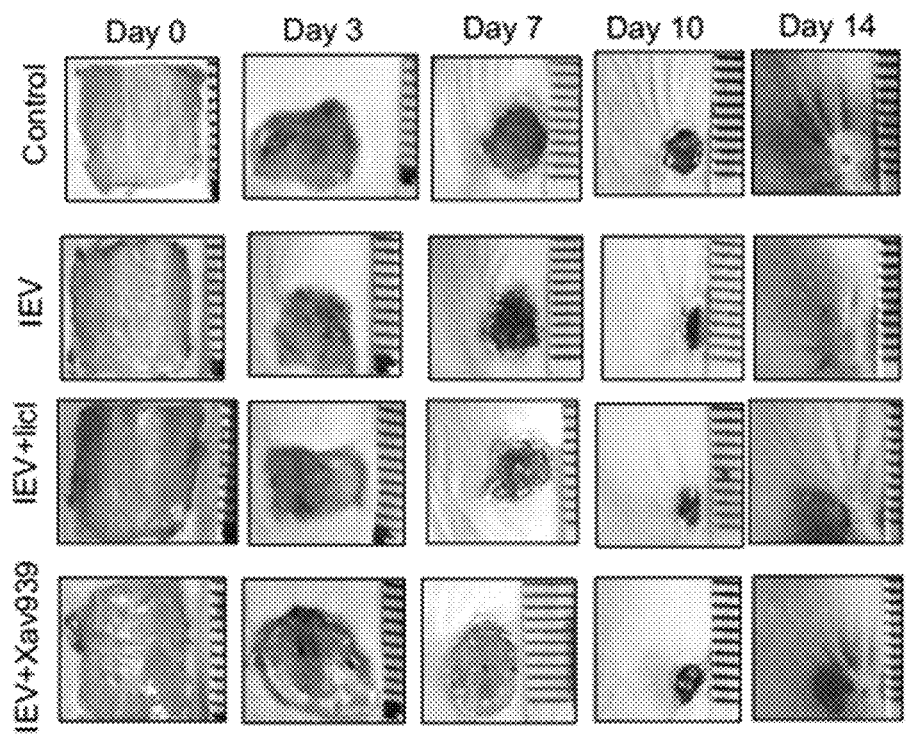
FIG. 15B shows the effects of different treatment groups on wound healing as described in Example 7.
Figure 15C:
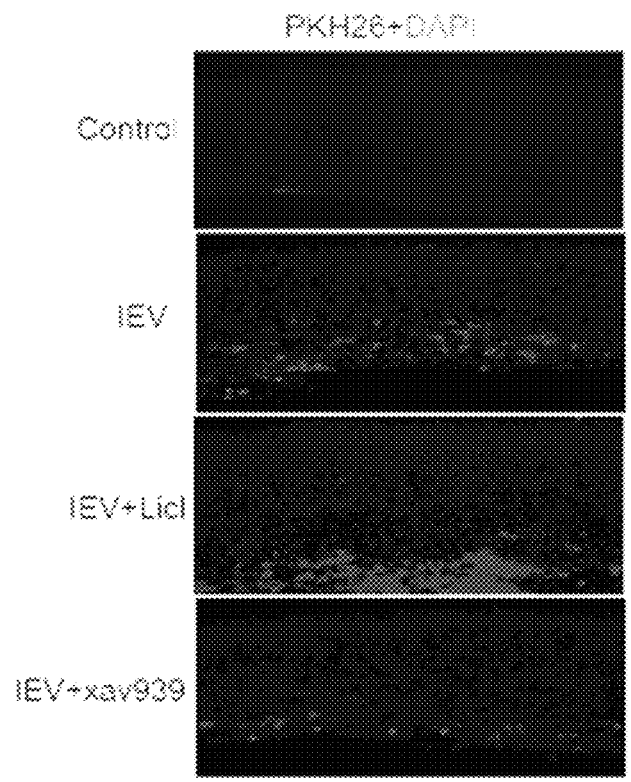
FIG. 15C shows the immunofluorescence analysis results of different treatment groups as described in Example 7.

A 1 cm×1 cm full-thickness wound was made in mice, and the effect of systemic injections of MSCs and IEVs on wound healing was examined. The results showed that both IEVs and MSCs promoted wound healing (FIG. 15A) with no significant difference. The Wnt agonist Licl accelerated the promotion of wound healing by IEVs, while the inhibitor XAV939 significantly attenuated the promotion of wound healing by IEVs. The immunofluorescence results showed that the Licl group had significantly increased IEVs accumulation in the wound site, and the XAV939 group had significantly decreased IEVs accumulation in the wound site, suggesting that the Wnt signaling pathways might affect wound healing by regulating the excretion of IEVs (FIG. 15B-C).

EXAMPLE 10 WRINKLE-REMOVING EFFECT OF LOCAL INJECTION OF IEVS

The IEVs were obtained as in Example 6.

The IEVs were introduced by intradermal injector. Principle of intradermal injection is as follows: by utilizing the negative pressure technology, the required substances can be accurately replenished at different depths of the skin. Before the microneedles enter the skin, the negative pressure instrument is used to lift the skin, and then multiple needles enter the deep epidermis. The injection dose and frequency can be adjusted. In addition, the pressure of the syringe is released before the needles come out, so there is no loss of nutrients.

The introduction steps are as follows:

A syringe was filled with the UCMSCs-derived IEVs prepared in step 9, and placed in a groove of the introduction instrument, and the injection depth was adjusted to 0.3 mm.

The subject was informed of the entire process, and confirmed the informed consent. The test site was disinfected, the needles of water-light injection instrument aimed at the test site (the chin) with the negative pressure turned on, and according to the operation procedures, the IEVs were injected into the test site.

Figure 16:
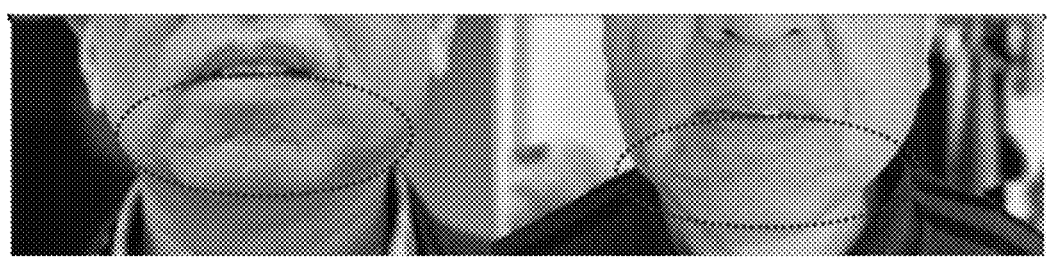
FIG. 16 shows a comparation of wrinkles in the chin area of a subject before and after the intradermal injection introduction IEVs as described in Example 10.

As shown in FIG. 16, after 50 days of intradermal injection (from Jan. 16, 2020 to Mar. 8, 2020), the wrinkles at the injection site were significantly reduced, indicating that the IEVs had good wrinkle-removing effect, and had a prospect for application in medical and medical cosmetology industries.

EXAMPLE 11 CULTURE OF INDUCED PLURIPOTENT STEM CELLS (IPS CELLS, IPSCS) AND PREPARATION OF IPSCS-DERIVED IEVS (1) Lentivirus Preparation 1 mL of DMEM was transferred to an EP tube, 5 μg of gene expression plasmid and 5 μg of g vsvg plasmid were added to 25 µl of liposomes, and the system was gently stirred at room temperature for 20 minutes. The mixture was added dropwise to cultured GP2-293 cells (95% mixed well) and vortexed to evenly distribute the mixture. The medium (DMEM+10% FBS+glutamine) was changed after 12 hours. After 24 hours of medium change, the medium containing the virus was collected, and after 48 hours the medium was collected again.

(2) Induction of Cellular Reprogramming

Each well (12-well plate) was inoculated with $5\times10^5$ GP2-293 cells cultured in step (1) at 80% confluence. 100 ng of virus was added to the culture medium (DMEM+10% FBS (heat inactivated)+glutamine) of 500-1000 µl/well, 4 µg/ml polybrene was added, and a new culture medium was changed after incubation for 12 h. The steps were repeated. Within 7 days, $5\times10^4$ induced cells were inoculated into 10 cm dishes with feeder cells (mEFs). The next day, the medium was changed to an Es medium with bFGF (4 ng/ml), and the medium was changed every other day. Five days later, the cells started to clone, and if there were no Es-like clones after 40 days, it was considered to be failed.

(3) Cell Passage

After 60% confluence, 0.5 ml of accutase was added to each dish and allowed to stand at room temperature for 1 minute. The separated cell aggregates were transferred to a 15 mL centrifuge tube, and an additional 2 mL mTeSR1 was used to collect any remaining aggregates. The rinse was added to the 15 ml tube. The 15 mL tube containing 200×g cell aggregates was centrifuged for 5 minutes at room temperature. The supernatant was aspirated. The cells were resuspended while ensuring that the cells remain aggregated. Human iPS cells were assembled with mTeSR1 on new plates coated with Matrigel. The culture dish was placed in an incubator at 37° C., and quickly moved left and right to evenly distribute the movement of aggregates. Incubation was carried out at 37° C. with 5% carbon dioxide and 95% humidity. The fluid was changed every day.

(4) Preparation of iPS-Derived IEVs

Figure 17:
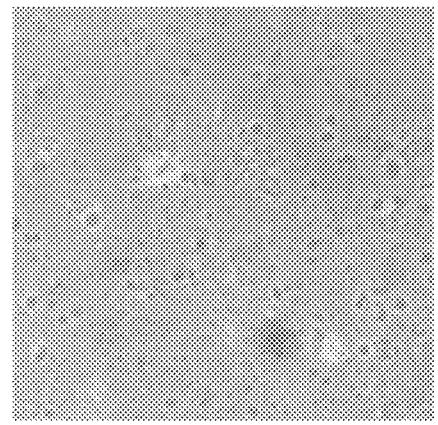
FIG. 17 shows iPSC-derived IEVs observed by electron microscopy in Example 11.

The preparation method is as in the Example 2
iPS cells (iPSCs) derived IEVs are shown in FIG. 17 under a light microscope at 400×.

EXAMPLE 12 IEVS DERIVED FROM STEM CELLS OF DIFFERENT DIFFERENTIATION POTENTIALS

A general experiment method is as follows:
Flow cytometry for apoptosis: human induced pluripotent stem cells (hiPSCs) of P26-P29 and human umbilical cord mesenchymal stem cells (hUCMSCs) of P7-P9 were induced to undergo apoptosis using Staurosporine (500 nM) for about 9 h, and stained with Annexin V (15 min) and 7AAD (3 min), and the apoptosis rate was detected by flow cytometry. In this example, hiPSCs of P26 (26th passage) and hUCMSCs of P7 (7th passage) were used.

Separation of IEVs and detection of Annexin V expression by flow cytometry: IEVs were prepared by differential centrifugation, including the following steps: centrifugation at 800 g for 10 min, followed by centrifugation at 2000 g for 5 min, followed by centrifugation at 16000 g for 30 min, followed by centrifugation at 30 min at 16000 g to obtain IEVs, and the IEVs were stained with Annexin V for 15 min and the subjected to flow cytometry.

Skin wound modeling: a square skin wound with a side length of 1.7 cm was made on the back of mice. IEVs (hiPSCs-IEVs, and hUCMSCs were injected at $6\times10^7$ by count per injection) were administered via the tail veins at Day 1, 4, 8, 12, respectively, and the wound size was photographed daily. Samples were taken at Day 14.

Figure 18:
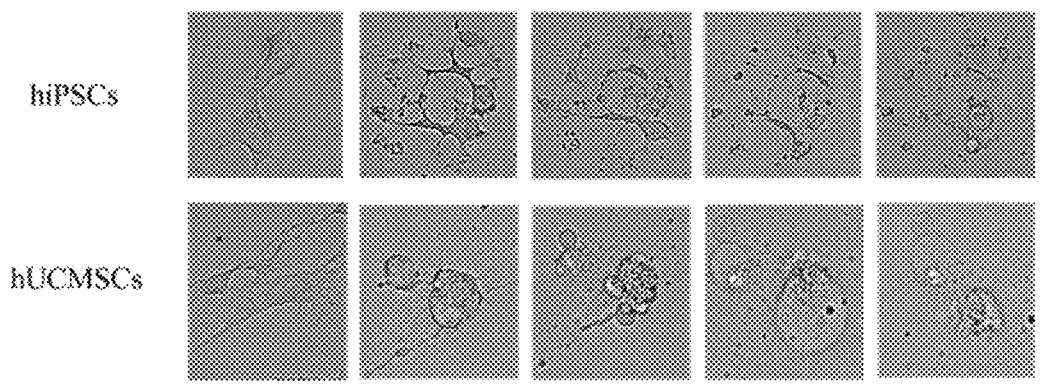
FIG. 18 shows the death processes of hiPSCs and hUCMSCs taken by a High Content Cellular Imaging Analysis System of Example 12.
Figure 19:
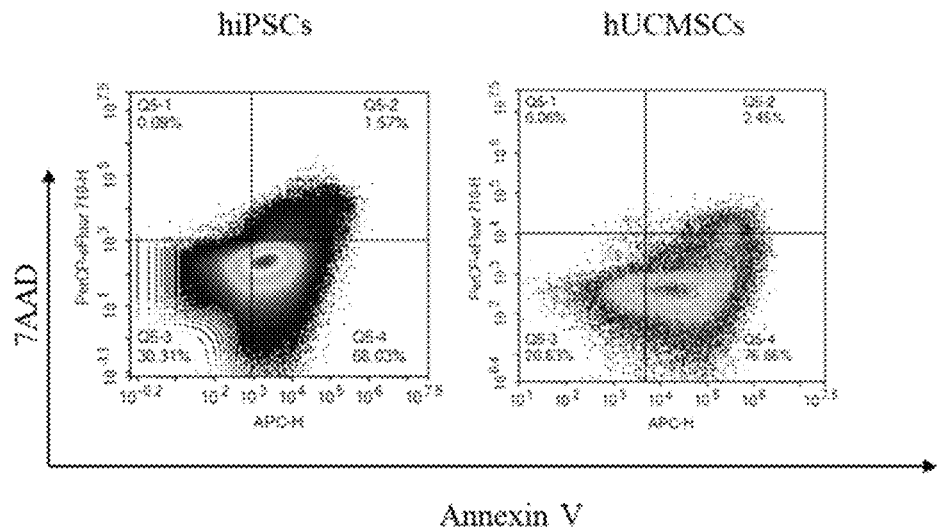
FIG. 19 shows flow cytometry of hiPSCs and hUCMSCs induced to apoptosis as described in Example 12.
Figure 20:
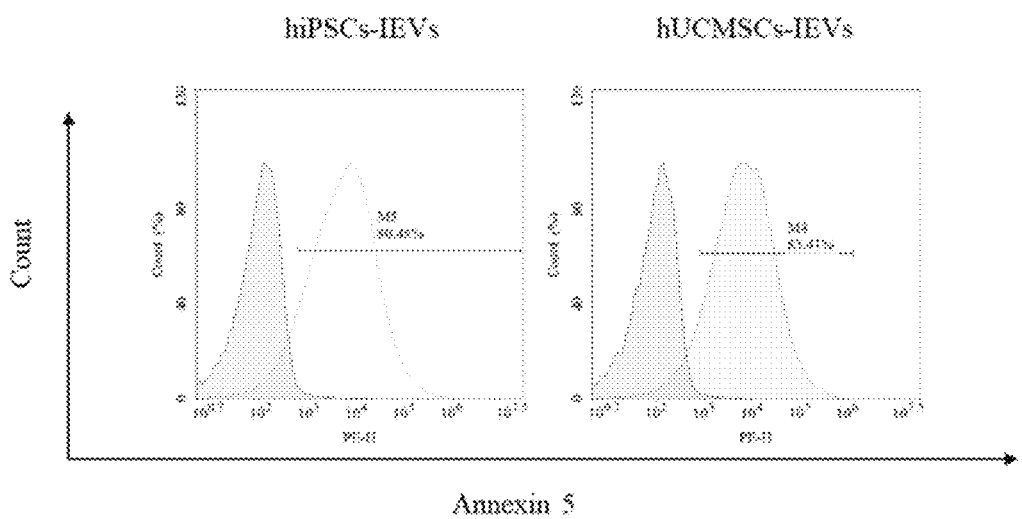
FIG. 20 shows the positive rates of Annexin 5 expressions by flow cytometry for hiPSCs and hUCMSCs as described in Example 12.

Results:
1. The death processes of hiPSCs and hUCMSCs were taken by a High Content Cellular Imaging Analysis System. As shown in FIG. 18, it was found that the two were have different death processes. hiPSCs contracted with multiple centers of the nucleus and cytoplasm, and then sent out dendritic branches with blebbing; while hUCMSCs contracted with a single center of the nucleus, accompanied by branching and blebbing.
2. As shown in FIG. 19, the apoptosis rates of hiPSCs and hUCMSCs induced to apoptosis were analyzed by flow cytometry, demonstrating that most cells underwent apoptosis.
3. As shown in FIG. 20, the positive rates of Annexin 5 expression of the above-mentioned IEVs obtained by differential centrifugation were over 80% by flow cytometry for both hiPSCs and hUCMSCs.
4. The two types of IEVs were characterized using Nanoparticle Tracking Analysis
4.1. As shown in FIG. 21, hiPSCs-IEVs had a particle size of about 100 nm, and hUCMSCs-IEVs had a particle size of about 180 nm;
4.2. As shown in FIG. 22, the yield of IEVs: 21971 particles/hiPSCs, 886 particles/hUCMSCs;
4.3. As shown in FIG. 23, the potential of hiPSCs-IEVs was about −12 mV, and the potential of hUCMSCs-IEVs was about −45 mV.
5. The in vivo repair and regeneration functions of the two cell-derived IEVs were compared using a skin wound model.

As shown in FIG. 24, the results showed that hiPSCs-IEVs significantly promoted wound healing, and hiPSCs-IEVs had a stronger tissue repair and regeneration function than hUCMSCs-IEVs.

In view of the many possible embodiments to which the principles of the disclosed invention may be applied, it should be recognized that the illustrated embodiments are only preferred examples of the disclosure and should not be taken as limiting the scope of the disclosure. Rather, the scope of the present disclosure is defined by the appended claims. We therefore claim all inventions that fall within the scope and spirit of these claims.

What is claimed is:

1. A method of treating a human in need of hair growth, comprising administering to the human in need thereof a therapeutically effective amount of an induced vesicle derived from a stem cell by inducing apoptosis of the stem cell in the presence of staurosporine to effectively regrow hair in the human in need thereof.

2. The method of claim 1, wherein the induced vesicle is an extracellular induced vesicle.

3. The method of claim 1, wherein the induced vesicle is selected from the group consisting of an exosome, a migrant, a microbubble, an apoptotic body, and an induced extracellular vesicle.

4. The method of claim 1, wherein the stem cell is selected from the group consisting of induced pluripotent stem cells, blood stem cells, bone marrow mesenchymal stem cells, urine mesenchymal stem cells, oral mesenchymal stem cells, adipose mesenchymal stem cells, placental mesenchymal stem cells, umbilical cord mesenchymal stem cells, periosteal mesenchymal stem cells, and skin mesenchymal stem cells.

5. The method of claim 1, wherein the stem cell is selected from the group consisting of induced pluripotent stem cells, umbilical cord mesenchymal stem cells, blood stem cells and bone marrow mesenchymal stem cells.

6. The method of claim 1, further comprising administering a skin medicament or a skin conditioner.

7. The method of claim 6, wherein the skin medicament and the skin conditioner are encapsulated in the induced vesicle.

8. The method of claim 1, wherein said administering of the induced vesicle comprises administering an injection, a tablet, a capsule, and a patch which comprises the induced vesicle.

9. The method of claim 1, further comprising administering an anti-aging substance or a positive regulator for Wnt signaling pathways.

10. The method of claim 9, wherein the anti-aging substance is metformin or resveratrol.

11. The method of claim 9, wherein the positive regulator for Wnt signaling pathways is selected from the group consisting of Licl, CHIR99021, SB-216763, BIO, Wnt Agonist and WAY 262611.

12. The method of claim 11, wherein the ratio of the vesicle and the anti-aging substance is $(0.5\text{-}5) \times 10^7$ by count: (0.05-10) mg.

* * * * *